US010758577B2

(12) United States Patent
Kazemi et al.

(10) Patent No.: US 10,758,577 B2
(45) Date of Patent: Sep. 1, 2020

(54) PROBIOTICS AND FERMENTATION METABOLITES FOR THE PREVENTION AND TREATMENT OF DISEASE CONDITIONS IN ANIMALS

(71) Applicant: PURE CULTURES, INC., Denver, CO (US)

(72) Inventors: Steven K. Kazemi, Denver, CO (US); Naseer Sangwan, Chicago, IL (US)

(73) Assignee: PURE CULTURES 2020, INC., Denver, CO (US)

( * ) Notice: Subject to any disclaimer, the term of this patent is extended or adjusted under 35 U.S.C. 154(b) by 14 days.

(21) Appl. No.: 16/220,416

(22) Filed: Dec. 14, 2018

(65) Prior Publication Data

US 2019/0192587 A1   Jun. 27, 2019

Related U.S. Application Data

(60) Provisional application No. 62/598,730, filed on Dec. 14, 2017.

(51) Int. Cl.

| | | |
|---|---|---|
| *A61K 35/747* | (2015.01) | |
| *A61P 31/04* | (2006.01) | |
| *A23L 33/135* | (2016.01) | |
| *A61K 9/16* | (2006.01) | |
| *C12P 19/04* | (2006.01) | |
| *A61P 1/00* | (2006.01) | |
| *A23K 50/75* | (2016.01) | |
| *A23K 50/40* | (2016.01) | |
| *A23K 50/10* | (2016.01) | |
| *A61K 35/744* | (2015.01) | |
| *A23K 10/18* | (2016.01) | |
| *A23K 50/30* | (2016.01) | |
| *A61K 45/06* | (2006.01) | |
| *A61K 35/00* | (2006.01) | |

(52) U.S. Cl.
CPC ............ *A61K 35/747* (2013.01); *A23K 10/18* (2016.05); *A23K 50/10* (2016.05); *A23K 50/30* (2016.05); *A23K 50/40* (2016.05); *A23K 50/75* (2016.05); *A23L 33/135* (2016.08); *A61K 9/16* (2013.01); *A61K 35/744* (2013.01); *A61K 45/06* (2013.01); *A61P 1/00* (2018.01); *A61P 31/04* (2018.01); *C12P 19/04* (2013.01); *A23V 2002/00* (2013.01); *A23Y 2220/03* (2013.01); *A23Y 2220/35* (2013.01); *A23Y 2220/67* (2013.01); *A23Y 2220/71* (2013.01); *A23Y 2280/15* (2013.01); *A23Y 2280/55* (2013.01); *A61K 2035/115* (2013.01)

(58) Field of Classification Search
CPC ...... A61K 35/747; A61K 9/16; A61K 35/744; A61K 45/06; A61K 2035/115; A61K 50/75; A61K 50/40; A61K 50/10; A61K 10/18; A61K 50/30; A61P 31/04; A61P 1/00; A23L 33/135; C12P 19/04; A23Y 2220/35; A23Y 2220/71; A23Y 2280/15; A23Y 2220/67; A23Y 2280/55; A23Y 2220/03

USPC ...................................................... 424/93.45
See application file for complete search history.

(56) References Cited

U.S. PATENT DOCUMENTS

| | | | |
|---|---|---|---|
| 8,168,171 B2 | 5/2012 | Mogna et al. | |
| 9,096,836 B2 | 8/2015 | Wood et al. | |
| 9,868,675 B2 | 1/2018 | Wallenstein et al. | |
| 10,053,392 B2 | 8/2018 | Wallenstein et al. | |
| 2004/0091537 A1* | 5/2004 | Miller | A61K 9/286 424/471 |
| 2016/0145163 A1 | 5/2016 | Wallenstein et al. | |
| 2016/0338361 A1 | 11/2016 | Smittle et al. | |
| 2016/0354417 A1* | 12/2016 | Smittle | A61K 36/064 |
| 2017/0020929 A1 | 1/2017 | Lin et al. | |
| 2018/0141878 A1 | 5/2018 | Wallenstein et al. | |
| 2019/0039963 A1 | 2/2019 | Wallenstein et al. | |

FOREIGN PATENT DOCUMENTS

| | | |
|---|---|---|
| CN | 103623293 | 3/2014 |
| KR | 20160143499 | 12/2016 |
| WO | WO 2016/124940 | 8/2016 |
| WO | WO 2017/105267 | 6/2017 |
| WO | WO 2017/132201 | 8/2017 |

OTHER PUBLICATIONS

International Search Report and Written Opinion dated Feb. 21, 2019 for related PCT application, PCT/US2018/065683 filed on Dec. 14, 2018 (17 pgs).
Plumed-Ferrer et al., "Comparative study of Sugar Fermentation and Protein Expression Patterns of Two *Lactobacillus Plantarum* Strains Grown in Three Different Media", Applied and Environmental Microbiology, Sep. 2008, vol. 74, No. 17, p. 5349-5358 (10 pgs).
Hijum et al., "Characterization of a Novel Fructosyltransferase from *Lactobacillus reuteri* that Synthesizes High-Molecular-Weight Inulin and Inulin Oligosaccharides", Applied and Environmental Microbiology, Sep. 2002, vol. 68, No. 9, p. 4390-4398 (9 pgs).
Higgins et al., "Effect of Lactic Acid Bacteria Probiotic Culture Treatment Timing on Salmonella Enteritidis in Neonatal Broilers", Poultry Science, 2010, vol. 89, p. 243-247 (5 pgs).
Skytta et al., "Production and Characterization of Antibacterial Compounds Produced by *Pediococcus damnosus* and *Pediococcus pentosaceus*", Journal of Applied Bacteriology 1993, vol. 74, p. 134-142 (9 pgs).
Zani, et al. "Effect of Probiotic CenBiot on the Control of Diarrhoea and Feed Efficiency in Pigs", Journal of Applied Microbiology, 1998, Vo. 84, p. 68-71 (4 pgs).

(Continued)

*Primary Examiner* — Jennifer M. H. Tichy
(74) *Attorney, Agent, or Firm* — Stinson LLP

(57) ABSTRACT

The present invention is directed to compositions comprising a mixture of microbes and the metabolites produced when the microbes are grown together. The invention is further directed to methods for making and using the compositions.

26 Claims, 11 Drawing Sheets

(56) References Cited

OTHER PUBLICATIONS

Aluwong et al., "Effect of Yeast Probiotic on Growth, Antioxidant Enzyme Activities and Malondialdehyde Concentration of Broiler Chickens", Antioxidants, 2013, vol. 2, p. 326-339 (14 pgs).

Prieto, et al., "Evaluation of the Efficacy and Safety of a Marine-Derived Bacillus Strain for Use as an In-Feed Probiotic for Newly Weaned Pigs", PLOS ONE, vol. 9, Issue 2, Feb. 2014, p. 1-12 (12 pgs).

Deng et al., "Gastrointestinal Tract Distribution of *Salmonella enteritidis* in Orally Infected Mice with a Species-Specific Fluorescent Quantitative Polymerase Chain Reaction", World Journal of Gastroenterology, Dec. 2007, vol. 13, No. 48, p. 6568-6574 (7 pgs).

2015 Sale of consortium product blen of *L. plantarum, L. acidophilus and L. fermentum* (This entry is for informational purposes only. No. documentation is being provided.).

Apr. 2017 sale of bluk single organism culture as an ingredient for dog kibble and human supplements product containing single organism *L. reuteri* PCR7 (This entry is for informational purposes only. No documentation is being provided.).

Jun. 2017 sale of bulk single organism culture as an ingredient for dog kibble and human supplements product containing single organism P. acidlactici PCLL01 and other nonmicrobial ingredients (This entry is for informational purposes only. No documentation is being provided.).

Jul. 2017 sale of bulk cultures containing freeze dried organism blend as ingredients for dog kibble and human supplements product containing P. acidlactici PCLL01 and L. reuteri PCR7 (This entry is for informational purposes only. No documentation is being provided.).

* cited by examiner

| Batch # | Fermentation strains | acetic acid ppm | propionic acid ppm | butyric acid ppm | ascorbic acid ppm | lactic acid bacteria count |
|---|---|---|---|---|---|---|
| 17011 1 | * | 2771 | 31.44 | 3.35 | 663 | $6.5 \times 10^{6}$ |
| 17011 2 | ** | 2336 | 39.65 | 3.45 | 343 | $3.9 \times 10^{7}$ |
| 17011 3 | *** | 2557 | 34 | 3.8 | 762 | $7.5 \times 10^{6}$ |

*Lactobacillus acidophilus, Lactobacillus fermentum, Pediococcus acidilactici, Enterococcus faecium

**Lactobacillus acidophilus, Lactobacillus reuteri, Pediococcus acidilactici, Enterococcus faecium

***Lactobacillus acidophilus, Lactobacillus reuteri, Lactobacillus fermentum, Pediococcus acidilactici

FIG. 3

PROBIOTICS AND FERMENTATION METABOLITES FOR THE PREVENTION AND TREATMENT OF DISEASE CONDITIONS IN ANIMALS

CROSS-REFERENCE TO RELATED APPLICATIONS

This application is based on and claims priority to U.S. Provisional Application Ser. No. 62/598,730, filed on Dec. 14, 2017, which is incorporated herein by reference in its entirety.

STATEMENT REGARDING FEDERALLY SPONSORED RESEARCH OR DEVELOPMENT

Not applicable.

STATEMENT REGARDING JOINT RESEARCH AGREEMENT

Not applicable.

BACKGROUND OF THE INVENTION

1. Field of the Invention

The present disclosure relates to probiotic microorganisms and fermentation metabolites produced thereby. In particular, the present disclosure relates to probiotics and fermentation metabolites that can be used to treat or prevent a disease or condition in animals.

2. Description of Related Art

Antibiotics have played an integral role in the animal food production industry as performance enhancement additives since the discovery of antibiotics in the early 1940s (McKenna, 2017). In most farms, antibiotics are used to treat clinical infections, control and prevent the spread of disease, and predominantly, to enhance animal growth (American Meat Institute, 2013). Field studies have shown that, when used as growth enhancers, antibiotics promote flock health by stabilizing the intestinal microbial flora, improving general performance and preventing intestinal pathologies (Hassan, 2010). For example, it has been shown that the use of tetracycline and tylosines at sub-therapeutic doses over long periods of time can increase the feed conversion ratio in poultry, swine, and cattle (Landers, 2012). These beneficial effects have pushed the industry towards antibiotic-centric production practices. Currently, in the United States, twelve classes of antibiotics may be used at different times in the life cycle of livestock many of which are analogs of human antibiotics (Landers, 2012). In 2012, over 30 million pounds of antibiotics were sold for animal use, more than four times the amount use for human health, underlying the important role of antibiotics in the food industry (Taillant, 2015). However as the use of antibiotics in food production has grown, considerable concerns associated with antibiotics have been identified. Notably, the widespread use of antibiotics can lead to the development of pathogens resistant to antibiotics.

BRIEF SUMMARY OF THE INVENTION

One aspect of the present disclosure is directed to a composition comprising at least two microbes and preferably the metabolites produced by the at least two microbes when grown in combination. In certain embodiments, the composition comprises at least two microbes selected from the group consisting of *Lactobacillus reuteri, Pediococcus acidilactici, Enterococcus faecium, Pediococcus pentosaceus, Lactobacillus acidophilus, Lactobacillus fermentum* and *Lactobacillus plantarum*; and preferably the metabolites produced by the at least two microbes when grown in combination.

Another aspect of the present disclosure is directed to a method of treating or preventing a disease or condition in an animal in need thereof. The method comprises administering to the animal a composition comprising at least two microbes and preferably the metabolites produced by the at least two microbes when grown in combination. In certain embodiments, the composition comprises at least two microbes selected from the group consisting of *Lactobacillus reuteri, Pediococcus acidilactici, Enterococcus faecium, Pediococcus pentosaceus, Lactobacillus acidophilus, Lactobacillus fermentum* and *Lactobacillus plantarum*; and preferably the metabolites produced by the at least two microbes when grown in combination. Other aspects and features of the present disclosure will be in part apparent and in part pointed out hereinafter.

BRIEF DESCRIPTION OF THE FIGURES

FIG. 3 is a table summarizing certain experimental results relating to the production of example compositions.

DETAILED DESCRIPTION OF PREFERRED EMBODIMENT

Figure 1:
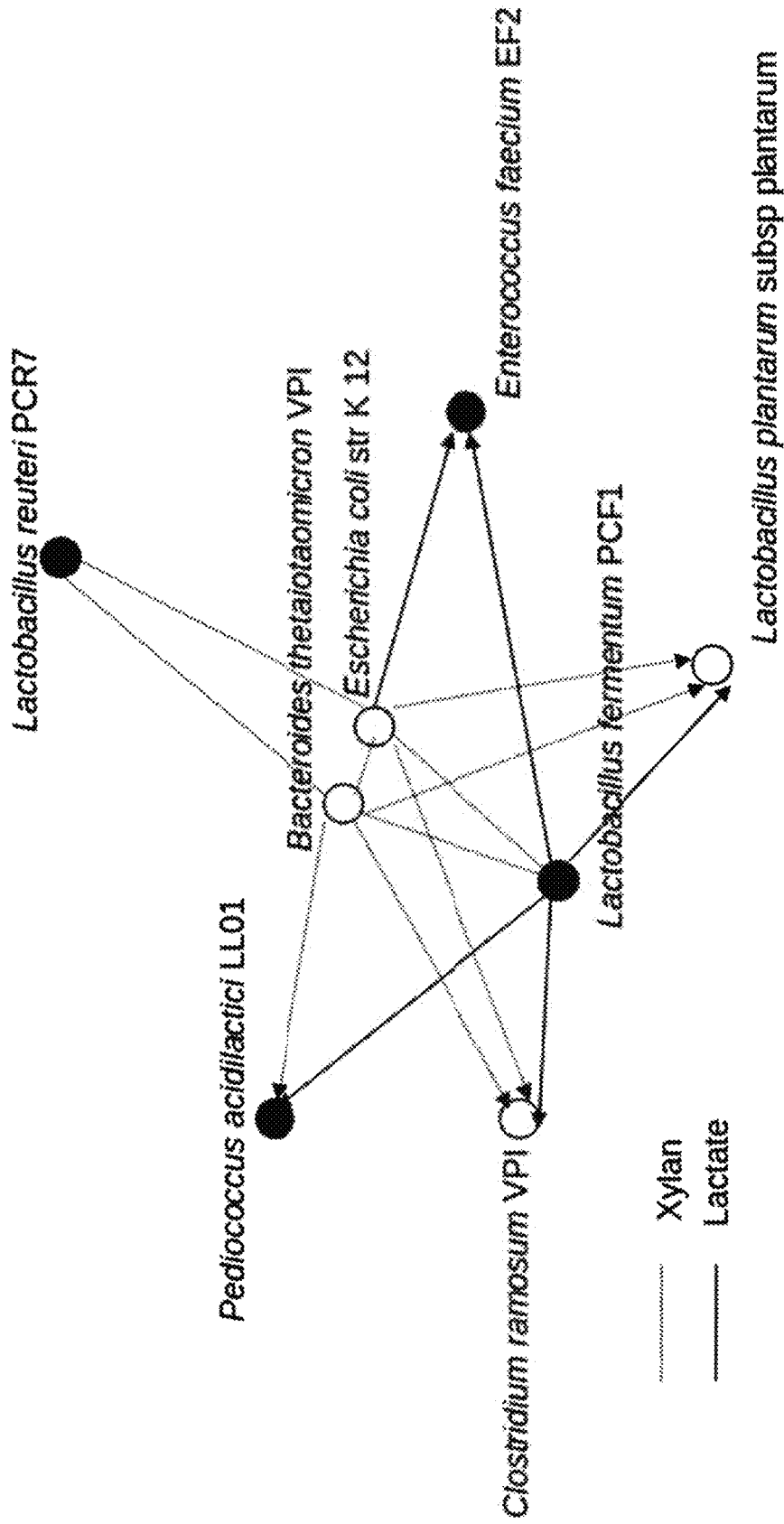
FIG. 1 is a diagram of an example cross-feeding model.
Figure 2:
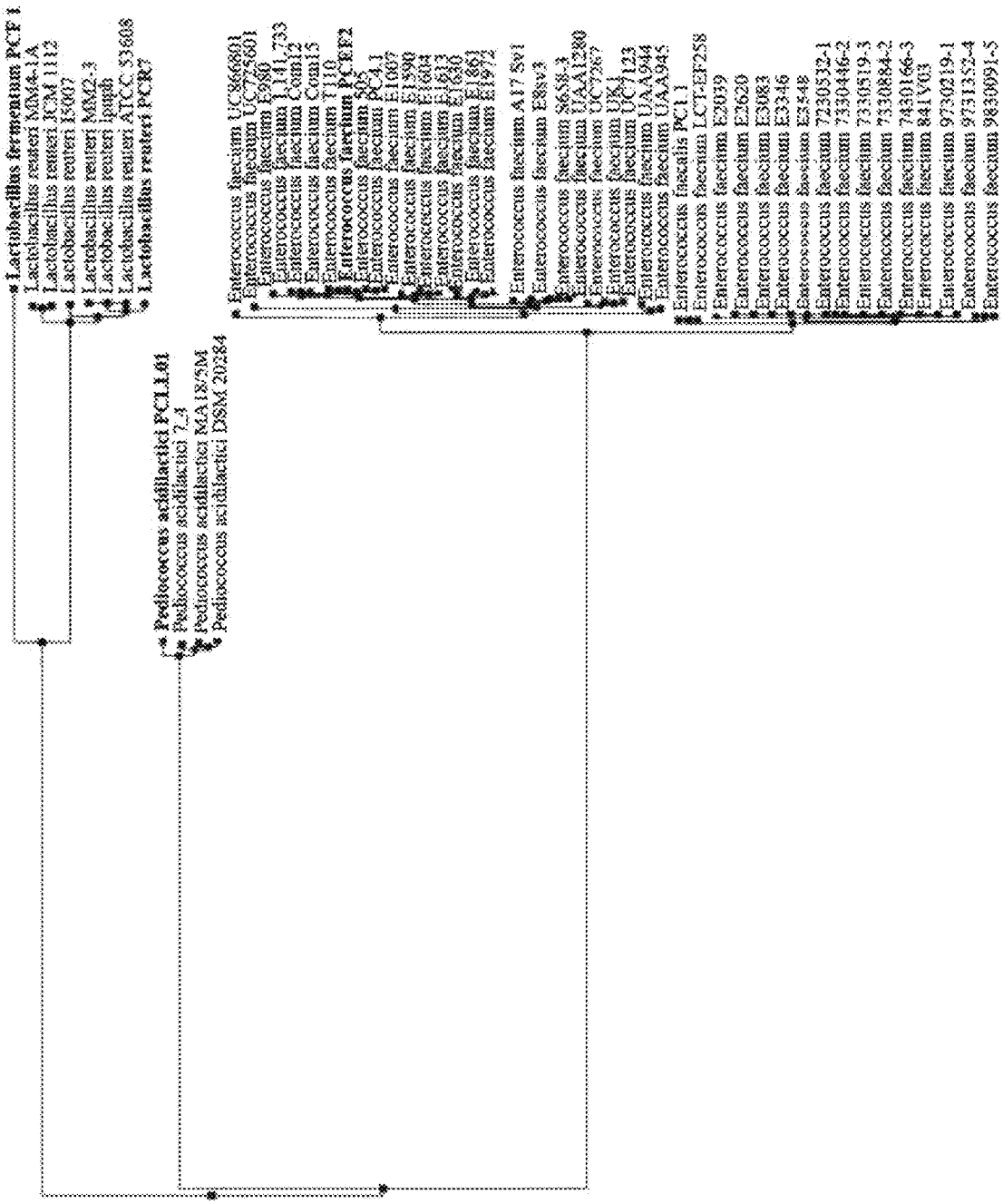
FIG. 2 is a diagram of an example phylogenetic tree.

Provided herein are methods and compositions for treating and preventing animal diseases or conditions. The compositions include probiotics, notably a mixture of at least two microbes. In certain embodiments, the microbes are selected from the group consisting of *Lactobacillus reuteri, Pediococcus acidilactici,* and *Enterococcus faecium.* In certain embodiments the composition additionally includes one or more of *Pediococcus pentosaceus, Lactobacillus acidophilus, Lactobacillus fermentum* and *Lactobacillus plantarum.* In certain embodiments, the compositions of the present invention comprise not only microbes, but fermentation products of the microbes when grown in combination, e.g. post-biotic metabolites, notably short chain fatty acids. Other aspects of the invention are directed to use of the compositions of the invention treat or prevent animal diseases or conditions.

It has been found that combinations of the microbes of present invention produce different fermentation products from the microbes when fermented alone and/or fermentation products in different ratios from the microbes when fermented alone. It has been further found that combinations of the microbes of the present invention, together with their unique mixture of fermentation metabolites, notably the short chain fatty acid metabolites, offer health benefits to animals. This is beneficial because, for example, the feed delivered to production animals is not the most effective for the animal to be converted into short chain fatty acids by the microbes of the present invention. By delivering a reliable and quantitative amount of the short chain fatty acid metabolites in the composition orally, directly to the animal, short chain fatty acids can be used indirectly in the production of pyruvate, acetyl-coenzyme A, or Acetyl-CoA. These are vital intermediates in the Krebs energy cycle. Further, the compositions of the present disclosure comprise ratios of short chain fatty acids that can be delivered in concentrations that are beneficial to the animal. By contrast, direct oral dosing of short chain fatty acids can limit absorption due to the fact that the amounts delivered can exceed the amounts an animal's gastrointestinal system is accustomed to receiving. It is further beneficial that administration of compositions of the present invention to an animal may reduce, or even eliminate, the need for antibiotics.

It has further been found that the compositions and fermentation metabolites of the present disclosure, such as short chain fatty acids, are heat stable and can tolerate the conditions of high heat during transit, storage, and pelletizing all common in the production animal feed system. The generation of heat stable beneficial fatty acids is therefore a benefit of the present invention in the agriculture industry and other industries.

I. Compositions

In an aspect, a composition of the disclosure comprises at least two microbes selected from the group consisting of *Lactobacillus reuteri, Pediococcus acidilactici, Enterococcus faecium, Pediococcus pentosaceus, Lactobacillus acidophilus, Lactobacillus fermentum* and *Lactobacillus plantarum*; and preferably the metabolites produced by the at least two microbes when grown in combination. In certain aspects, the at least two microbes are selected from the group consisting of *Lactobacillus reuteri, Pediococcus acidilactici,* and *Enterococcus faecium*; preferably together with probiotic fermentation products of the microbes when grown in combination, notably short chain fatty acids. In certain embodiments the composition additionally includes one or more microbes selected from the group consisting of *Pediococcus pentosaceus, Lactobacillus acidophilus, Lactobacillus fermentum* and *Lactobacillus plantarum.* In certain embodiments the compositions of the disclosure comprise at least one microbe selected from the group consisting of *Lactobacillus reuteri, Pediococcus acidilactici,* and *Enterococcus faecium* and at least one microbe selected from the group consisting of *Pediococcus pentosaceus, Lactobacillus acidophilus, Lactobacillus fermentum* and *Lactobacillus plantarum,* preferably together with probiotic fermentation products of the microbes when grown in combination, notably short chain fatty acids.

In certain embodiments the composition comprises *Lactobacillus reuteri, Pediococcus acidilactici,* and *Enterococcus faecium; Lactobacillus reuteri, Pediococcus acidilactici, Enterococcus faecium* and *Pediococcus pentosaceus; Lactobacillus reuteri, Pediococcus acidilactici, Enterococcus faecium* and *Pediococcus pentosaceus* and *Lactobacillus fermentum; Lactobacillus reuteri, Pediococcus acidilactici,* and *Lactobacillus acidophilus;* or *Lactobacillus reuteri, Pediococcus acidilactici, Enterococcus faecium* and *Lactobacillus acidophilus;* in each case preferably together with probiotic fermentation products of the microbes when grown in combination, notably short chain fatty acids.

In certain embodiments, the composition comprises at least two microbes selected from the group consisting of *Lactobacillus reuteri, Pediococcus acidilactici, Enterococcus faecium, Pediococcus pentosaceus, Lactobacillus acidophilus, Lactobacillus fermentum* and *Lactobacillus plantarum*; preferably together with their metabolites when grown in combination, notably short chain fatty acids. Exemplary compositions of the present invention include, but are not limited to compositions comprising the following; *Lactobacillus reuteri* and *Pediococcus acidilactici; Lactobacillus reuteri* and *Enterococcus faecium; Lactobacillus reuteri* and *Pediococcus pentosaceus; Pediococcus acidilactici* and *Enterococcus faecium; Pediococcus acidilactici* and *Pediococcus pentosaceus; Enterococcus faecium* and *Pediococcus pentosaceus; Lactobacillus reuteri, Pediococcus acidilactici,* and *Enterococcus faecium; Lactobacillus reuteri, Pediococcus acidilactici,* and *Pediococcus pentosaceus; Pediococcus acidilactici, Enterococcus faecium* and *Pediococcus pentosaceus; Lactobacillus reuteri* and *Lactobacillus acidophilus; Pediococcus acidilactici* and *Lactobacillus acidophilus; Enterococcus faecium* and *Lactobacillus acidophilus; Lactobacillus reuteri, Pediococcus acidilactici,* and *Lactobacillus acidophilus;* and *Pediococcus acidilactici, Enterococcus faecium* and *Lactobacillus acidophilus; Lactobacillus reuteri* and *Lactobacillus acidophilus; Lactobacillus reuteri* and *Lactobacillus reuteri; Lactobacillus reuteri* and *Lactobacillus plantarum; Enterococcus faecium* and *Lactobacillus acidophilus; Enterococcus faecium* and *Lactobacillus fermentum; Enterococcus faecium* and *Lactobacillus plantarum; Pediococcus pentosaceus* and *Lactobacillus acidophilus; Pediococcus pentosaceus* and *Lactobacillus fermentum; Pediococcus pentosaceus* and *Lactobacillus plantarum; Pediococcus acidilactici* and *Lactobacillus acidophilus; Pediococcus acidilactici* and *Lactobacillus fermentum; Pediococcus acidilactici* and *Lactobacillus plantarum; Lactobacillus acidophilus* and *Lactobacillus fermentum; Lactobacillus acidophilus* and *Lactobacillus plantarum;* or *Lactobacillus fermentum* and *Lactobacillus plantarum;* in each case alone or in combination with additional microbes selected from the group consisting of *Lactobacillus reuteri, Pediococcus acidilactici, Enterococcus faecium, Pediococcus pentosaceus, Lactobacillus acidophilus, Lactobacillus fermentum* and *Lactobacillus plantarum*; in each case preferably together with probiotic fermentation products of the microbes when grown in combination, notably short chain fatty acids.

In each of the embodiments discussed above, one or more of the following strains may be used: *Lactobacillus reuteri* PCR7, *Pediococcus acidilactici* PCLL01, *Enterococcus faecium* PCEF02, *Pediococcus pentosaceus* PCPP01, *Lactobacillus fermentum* PCF01 and a commercially available *Lactobacillus acidophilus* PCLA18. Certain embodiments of the present invention comprise a combination of *Lactobacillus reuteri* PCR7, *Pediococcus acidilactici* PCLL01, *Enterococcus faecium* PCEF02, and *Pediococcus pentosaceus* PCPP01; or *Lactobacillus reuteri* PCR7, *Pediococcus acidilactici* PCLL01, *Enterococcus faecium* PCEF02, *Pediococcus pentosaceus* PCPP01 and *Lactobacillus fermentum* PCF01, preferably together with probiotic fermentation products of the microbes when grown in combination. The strain of *E. faecium*, such as PCEF02, preferably has low toxicity, acceptable for the intended use.

It has been found that combinations of the microbes of the present invention produce different fermentation products from the microbes when fermented alone. In addition, certain of the microbes may be present in reduced numbers after fermentation due to competition among the microbes during the fermentation process. As detailed in Example 14, a composition comprising *Lactobacillus reuteri*, *Pediococcus acidilactici*, *Enterococcus faecium*, and *Pediococcus pentosaceus* produces different fermentation metabolites from the individual microbes. Other combinations of microbes producing different fermentation products are listed in the table below.

TABLE 1

| | | Fermentation Products | | | |
|---|---|---|---|---|---|
| Formulation | Key peaks | Acetic Acid (ppm) | Propionic acid (ppm) | Butryric acid (ppm) | Enumeration |
| 17010: PCLA18, PCLF01, PCLL01 | 6 peaks | 2760.05 | 31.81 | 20.62 | |
| 17011 1: PCLA18, PCLF01, PCLL01, PCEF02 | 10 peaks | 2872.50 | 31.44 | 3.35 | $6.5 \times 10^6$ |
| 17011 2 USDA #1: PCLA18, PCLL01, PCEF02, PCR7 | 8 peaks | 2336 | 39.65 | 3.45 | $3.9 \times 10^7$ |
| 17001 3: PCLA18, PCLF01, PCLL01, PCR7 | 5 peaks | 2557.70 | 34.43 | 3.8 | $7.5 \times 10^6$ |

In an embodiment, the composition may further comprise one or more additional species of microorganisms from the genera selected from *Pediococcus*; *Lactobacillus*; *Lactococcus*; *Bifidobacterium*; *Leuconostoc*; *Streptococcus*; and *Bacillus*.

In an additional embodiment, the composition may further comprise one or more of the species of microorganisms selected from the group consisting of *Pediococcus pentosaceus*; *Lactobacillus acidophilus*; *Lactobacillus plantarum*; *Lacotobacillus rhamnosus*; *Lactobacillus fermentum*; *Lactobacillus bifidus*; *Lactobacillus brevis*; *Lactobacillus bulgaricus*; *Lactobacillus casei*; *Lactobacillus delbrueckii*; *Lactobacillus rhamnosus*; *Lactobacillus helveticus*; *Lactobacillus johnsonii*; *Lactobacillus lactis*; *Lactobacillus lactis* ssp. *Cremoris*; *Lactobacillus lactis* ssp. *Lactis*; *Lactobacillus paracase*; *Lactococcus cremoris*; *Lactococcus lactis*; *Lactococcus lactis* ssp. *Cremoris*; *Bifidobacterium infantis*; *Bifidobacterium lactis*; *Bifidobacterium animalis*; *Bifidobacterium bifidum*, *Bifidobacterium longum*; *Bifidobacterium breve*; *Leuconostoc mesenteroides* ssp *mesenteroides*; *Leuconostoc mesenteroides* ssp *cremoris*; *Streptococcus bovis*; *Streptococcus salivarius*; *Streptococcus salivarius* ssp. *Thermophilus*; *Bacillus coagulans*; *Bacillus amyloliquefaciens*; *Bacillus licheniformis*; *Bacillus subtilis*; and *Bacillus lentus*.

In each of the embodiments discussed above, one or more of the following strains may be used: *Lactobacillus reuteri* PCR7, *Pediococcus acidilactici* PCLL01, *Enterococcus faecium* PCEF02, *Pediococcus pentosaceus* PCPP01, *Lactobacillus fermentum* PCF01 and a commercially available *Lactobacillus acidophilus* PCLA18.

The microorganisms included in the compositions of the present disclosure may be obtained from a collection of microorganisms, such as the American Type Culture Collection (ATCC) or purchased from commercial vendors of microbial or probiotic strains. In accordance herewith the microorganisms are then cultured in a fermentation medium under suitable conditions to grow the microorganisms. Certain proprietary microorganisms have been deposited with the Agricultural Research Service Culture Collection NRRL Northern Research Service Culture Collection Research Laboratory, 1815 N. University Street, Peoria, Ill. 61604, in accord with the Budapest Treaty on Dec. 3, 2018, as shown in the following table.

TABLE 2

| | | NRRL numbers | |
|---|---|---|---|
| # | NRRL # | Pure Cultures Strain # | Genius/species |
| 1 | B-67717 | PCLL01 | *Pediococcus acidilacticia* |
| 2 | B-67718 | PCR7 | *Lactobacillus reuteri* |
| 3 | B-67719 | PCPP01 | *Pediococcus pentosaceus* |
| 4 | B-67720 | PCEF02 | *Enterococcus faecium* |
| 5 | B-67701 | PCLA18 | *Lactobacillus acidophilus* |

A. Fermentation Process

Many probiotic products on the market simply provide a single microbe or combination of microbes. However, in certain embodiments of the present invention, the compositions of the present invention are produced by first fermenting the combinations of microbes in a suitable fermentation medium to produce metabolites or "postbiotics" that are included in the composition.

In an embodiment, for example, a composition comprising at least two microbes selected from the group consisting of *Lactobacillus reuteri, Pediococcus acidilactici,* and *Enterococcus faecium,* and optionally one or more of *Pediococcus pentosaceus, Lactobacillus acidophilus, Lactobacillus fermentum* and *Lactobacillus plantarum,* including any of the compositions described in more detail above, may be added to a fermentation media and grown. Further, the at least two microbes may produce metabolites that are included in the composition.

Suitable fermentation media may include media comprising, for example, molasses, such as a molasses based on sugar beet juice, sugar cane juice, sucrose, dextrose, glucose, corn steep solids, or corn steep liquor.

In an embodiment, the amount of molasses in the fermentation media may be from about 1% v/v to about 10% v/v. In some embodiments, the amount of molasses in the fermentation media may be about 1% v/v, about 2% v/v, about 3% v/v, about 4% v/v, about 5% v/v, about 6% v/v, about 7% v/v, about 8% v/v, about 9% v/v, or about 10% v/v.

In some embodiments the fermentation medium may include molasses in higher amounts. In some embodiments, the fermentation medium may include molasses:water at a ratio of from about 20:80 v/v to about 35:65 v/v. In other embodiments, the fermentation medium may include molasses at a ratio of about 20:80 v/v, about 25:75 v/v, about 30:70 v/v, or about 35:65 v/v.

The fermentation media may also comprise formulation agents, for example, one or more exogenous prebiotic agents, such as fructooligosaccharide (FOS), a galactooligosaccharide, a xylooligosaccharides, an isomaltooligosaccharides, an inulin oligosaccharide, glucooligosaccharides, soybean oligosaccharides, lactosucrose, palatinose, erythritol, or a mannanoligosaccharide to prepare a liquid formulation or a solid formulation, for example about 5%.

The fermentation media may also comprise glycerol, for example about 0.5% to 3% of the fermentation media.

In certain embodiments the disclosed invention comprises a composition comprising at least two microbes selected from the group consisting of *Lactobacillus reuteri, Pediococcus acidilactici,* and *Enterococcus faecium,* and optionally one or more of *Pediococcus pentosaceus, Lactobacillus acidophilus, Lactobacillus fermentum* and *Lactobacillus plantarum,* including any of the compositions described in more detail above, added to a fermentation media comprising molasses, and optionally glycerol, in any of the concentrations above and grown to produce metabolites. In certain embodiments, a composition comprising *Lactobacillus reuteri* and *Pediococcus acidilactici; Lactobacillus reuteri, Pediococcus acidilactici* and *Lactobacillus acidophilus; Lactobacillus reuteri, Pediococcus acidilactici,* and *Enterococcus faecium; Lactobacillus reuteri, Pediococcus acidilactici, Enterococcus faecium* and *Pediococcus pentosaceus; Lactobacillus reuteri, Pediococcus acidilactici, Enterococcus faecium* and *Pediococcus pentosaceus* and *Lactobacillus fermentum*; or *Lactobacillus reuteri, Pediococcus acidilactici, Enterococcus faecium* and *Lactobacillus acidophilus* is added to a fermentation media comprising molasses in any of the concentrations above, and optionally containing glycerol, inulin and/or FOS, and grown to produce metabolites. In certain embodiments, a weak media, having low amounts of molasses, and optionally glycerol, is used while still producing a composition with sufficient microbes and metabolites to treat or prevent a disease or condition. In certain embodiments, one or more of the following strains is be used: *Lactobacillus reuteri* PCR7, *Pediococcus acidilactici* PCLL01, *Enterococcus faecium* PCEF02, *Pediococcus pentosaceus* PCPP01, *Lactobacillus fermentum* PCF01 and a commercially available *Lactobacillus acidophilus* PCLA18.

The fermentation media may also comprise a nitrogen source, a protein source, a trace element, vitamin, a buffering agent, or other components.

In an embodiment, the fermentation media may include a nitrogen source. Suitable nitrogen sources include, without limit, yeast extract, alanine, arginine, asparagine, aspartic acid, glutamine, isoleucine, ammonia citrate, serine, valine, and ammonia sulfate, ammonia salts, whey extract, skim milk powder, corn steep liquor or solids, soya bean meal, broadbean peptone, corn peptone, pea peptone, wheat peptone, potato peptone, hydrolysate of casein, lupin peptone, malt extract, meat peptone and rice peptone. In certain embodiments the nitrogen source can be 1 to 15% of the formulation.

In an embodiment, the fermentation process may include the use of agents such as Ammonia hydroxide, sodium hydroxide, sodium carbonate, calcium carbonate to be used as pH control.

In an embodiment, the fermentation media may include a protein source. Suitable protein sources include, without limit, a soy extract, a yeast extract, a pea extract, broadbean extract, corn extract, a potato extract, a dairy extract, skim milk power, a tapioca extract, malt extract, meat extract, malt extract and a rice extract. In certain embodiments the protein source can be 1 to 15% of the formulation.

In an embodiment, the fermentation media may include a trace element. Suitable trace elements include, without limit, iron, zinc, copper, manganese, magnesium, molybdenum, and cobalt.

Typical ranges for trace elements are set forth in the following table.

TABLE 3

Trace Elements

| Component | Range (g/L) |
|---|---|
| $KH_2PO_4$ | 1.0-4.0 |
| $MgSO_4 *7H_2O$ | 0.25-3.0 |
| KCL | 0.5-12.0 |
| $CaCO_3$ | 1.5-17.0 |
| $FeSO_4$ | 0.01-0.1 |
| $ZnSO_4$ | 0.1-1.0 |
| $MnSO_4$ | 0.01-0.1 |
| CuSO | 0.003-0.01 |
| $NaMoO_4*2H_2O$ | 0.01-0.1 |

Table reprinted from Principles of fermentation Technology P. F. Stanbury, A. Whitaker and S. J. Hall second Edition p. 103

In an embodiment, the fermentation media may include a buffering agent. Suitable buffering agents include, without limit, potassium diphosphate, potassium phosphate, sodium carbonate, sodium bicarbonate, potassium carbonate, and potassium bicarbonate.

Typical ranges of buffering agents are set forth in the following table.

TABLE 4

Buffering Agents

| Component | Range (g/L) |
|---|---|
| Dipotassium Phosphate dibasic | 1-5 |
| Citric acid | 0.5-2.5 |
| Monosodium citrate | 0.5-10 |
| Disodium citrate | 0.5-10 |
| Trisodium citrate | 0.5-10 |

TABLE 4-continued

Buffering Agents

| Component | Range (g/L) |
| --- | --- |
| Sodium carbonate | 0.5-5 |
| Calcium carbonate | 0.5-5 |
| Sodium hydroxide | Used to titrate pH into more basic range |
| Ammonium hydroxide | Used to titrate pH into more basic range |

In some embodiments, the fermentation medium contains peptone, beef extract, yeast extract, glucose, sodium acetate, polysorbate 80, dipotassium hydrogen phosphate, ammonium acetate, magnesium sulfate, and manganese sulfate.

In some embodiments, the fermentation medium contains from about 0.5% to about 2.5% caseine peptone, from about 0.5% to about 3.5% beef extract, from about 0.1% to about 3.5% yeast extract, from about 1.0% to about 5.0% glucose, from about 0.1% to about 5.0% sodium acetate, about 0.05% to about 0.5% polysorbate 80, from about 0.05% to about 0.5% dipotassium hydrogen phosphate, from about 0.05% to about 0.5% ammonium acetate, from about 0.005% to about 0.1% magnesium sulfate, and from about 0.0005 to about 0.01% manganese sulfate.

In some embodiments, the fermentation medium may be modified including, for example, by replacing casein peptone with pea peptone, soy peptone, or potato peptone, corn peptone, broadbean peptone, and meat peptone.

In some embodiments, the fermentation medium prior to initiating growth of the microorganisms can comprise the amino acid lysine, which, without being bound by theory, may enhance the production of the short chain fatty acid butyrate.

In certain embodiments the disclosed invention comprises a composition comprising at least two microbes selected from the group consisting of *Lactobacillus reuteri*, *Pediococcus acidilactici*, and *Enterococcus faecium*, and optionally one or more of *Pediococcus pentosaceus, Lactobacillus acidophilus, Lactobacillus fermentum* and *Lactobacillus plantarum*, including any of the compositions described in more detail above, added to a fermentation media comprising molasses in any of the concentrations above, and optionally glycerol.

Suitable fermentation conditions include a temperature range of from about 25° C. to about 42° C. In some embodiments, the fermentation temperature may be about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., or about 42° C.

Typical fermentation times range from 18 to 50 hours. The target fermentation time is based on a combination of pH, OD reading, total acidity and alkanlinity of solution.

The vessel in which the microorganisms are cultivated is either held at anaerobic or aerobic conditions.

B. Formulation

In some embodiments, upon conclusion of microbial growth the medium and cells may be formulated into a formulation comprising the probiotic microorganisms together with fermentation metabolites produced by the microorganisms, which may include one or more of produced short chain fatty acids, sugars, oligosaccharides, or bacteriocins. In certain embodiments, the formulation comprises secondary and/or tertiary metabolites. In addition, certain of the microbes may be reduced in number in the fermentation product due to competition between microbes during the fermentation process. The formulations may be in liquid or solid forms.

In an embodiment, the metabolites may include a short chain fatty acid. Suitable short chain fatty acids include, without limit, acetic acid, formic acid, propionic acid, butyric acid, isobutyric acid, valeric acid, succinic and isovaleric acid.

The microorganisms during growth produce substantial quantities of short chain fatty acids in the fermentation medium, for example in the range of about 0.5 mg/mL to about 30.0 mg/mL. In some embodiments, the amount of short chain fatty acids produced in the fermentation medium may be about 0.5 mg/mL, about 1.0 mg/mL, about 1.5 mg/mL, about 2.0 mg/mL, about 2.5 mg/mL, about 3.0 mg/mL, about 3.5 mg/mL, about 4.0 mg/mL, about 4.5 mg/mL, about 5.0 mg/mL, about 5.5 mg/mL, about 6.0 mg/mL, about 6.5 mg/mL, about 7.0 mg/mL, about 7.5 mg/mL, about 8.0 mg/mL, about 8.5 mg/mL, about 9.0 mg/mL, about 9.5 mg/mL, about 10.0 mg/mL, about 10.5 mg/mL, about 11.0 mg/mL, about 11.5 mg/mL, about 12.0 mg/mL, about 12.5 mg/mL, about 13.0 mg/mL, about 13.5 mg/mL, about 14.0 mg/mL, about 14.5 mg/mL, about 15.0 mg/mL, about 15.5 mg/mL, about 16.0 mg/mL, about 16.5 mg/mL, about 17.0 mg/mL, about 17.5 mg/mL, about 18.0 mg/mL, about 18.5 mg/mL, about 19.0 mg/mL, about 19.5 mg/mL, about 20.0 mg/mL, about 20.5 mg/mL, about 21.0 mg/mL, about 21.5 mg/mL, about 22.0 mg/mL, about 22.5 mg/mL, about 23.0 mg/mL, about 23.5 mg/mL, about 24.0 mg/mL, about 24.5 mg/mL, about 25.0 mg/mL, about 25.5 mg/mL, about 26.0 mg/mL, about 26.5 mg/mL, about 27.0 mg/mL, about 27.5 mg/mL, about 28.0 mg/mL, about 28.5 mg/mL, about 29.0 mg/mL, about 29.5 mg/mL, or about 30.0 mg/mL.

In another embodiment, the metabolites may include a sugar. Suitable sugars include, without limit, a 4-carbon sugar, a 5-carbon sugar, and a 6-carbon sugar. Suitable 4-carbon sugars include, without limit, erythrose and threose. Suitable 5-carbon sugars include, without limit, ribose, arabinose, xylose, and lyxose. Suitable 6-carbon sugars include, without limit, glucose, galactose, mannose, allose, altrose, gulose, idose, and talose. Such metabolites are generally produced as intermediate metabolites that are consumed by the microbes during the fermentation process to produce the final metabolites contained in the compositions of the present invention.

In another embodiment, the metabolites may include an oligosaccharide. Suitable oligosaccharides include, without limit, fructooligosaccharide, galactooligosaccharide, xylooligosaccharides, erythritol, palatinose, isomaltooligosaccharides, and mannanoligosaccharide. Certain oligosaccharides "prebiotics" are consumed by the bacteria during the fermentaiton process. Some new "prebiotics" are formed by the bacteria during the fermentation process.

In still another embodiment, the metabolites may include a bacteriocin. Suitable bacteriocins include, without limit, acidophilin, acidolin, and reutericin.

Yet other fermentation metabolites that can be produced include peptides, functional proteins, enzymes, amino acids, hydrogen sulfide, hydrogen peroxide, alcohol, carbon dioxide, sulfur dioxide, polyphenols, mannitol, and vitamins.

In some embodiments, upon conclusion of microbial growth the obtained compositions, i.e., the growth medium, including the probiotic microorganisms and fermentation metabolites, may be used directly to prevent or treat a disease or condition in animals. In some embodiments, upon conclusion of growth, the medium and cells may be prepared to obtain a liquid or solid formulation comprising the composition. Thus, for example, the compositions may be included directly into the water supply of animals.

In an embodiment, the compositions disclosed herein, comprising at least two microbes selected from the group consisting of *Lactobacillus reuteri*, *Pediococcus acidilactici*, and *Enterococcus faecium*, and optionally one or more of *Pediococcus pentosaceus*, *Lactobacillus acidophilus*, *Lactobacillus fermentum* and *Lactobacillus plantarum*, including any of the compositions described in more detail above, and the metabolites produced by the at least two microbes when grown in combination, may be formulated as a liquid or a solid.

Certain embodiments of the invention comprise the compositions disclosed herein, comprising at least two microbes selected from the group consisting of *Lactobacillus reuteri*, *Pediococcus acidilactici*, and *Enterococcus faecium*, and optionally one or more of *Pediococcus pentosaceus*, *Lactobacillus acidophilus*, *Lactobacillus fermentum* and *Lactobacillus plantarum*, including any of the compositions described in more detail above, and the metabolites produced by the at least two microbes when grown in combination in a medium comprising molasses, and optionally glycerol, inulin and/or FOS as described above.

In certain embodiments, a composition comprises *Lactobacillus reuteri* and *Pediococcus acidilactici Lactobacillus reuteri*, *Pediococcus acidilactici*, and *Enterococcus faecium*; *Lactobacillus reuteri*, *Pediococcus acidilactici*, *Enterococcus faecium* and *Pediococcus pentosaceus*; or *Lactobacillus reuteri*, *Pediococcus acidilactici*, *Enterococcus faecium* and *Lactobacillus acidophilus* and the metabolites produced by the microbes when grown together in a medium comprising molasses in any of the concentrations above, and optionally glycerol, inulin and/or FOS.

It has been found that combinations of the microbes of the present invention, together with their unique mixture of fermentation metabolites, notably the short chain fatty acid metabolites, offer health benefits to animals, as discussed in more detail in Examples 12-14.

Formulation as a liquid or solid may be achieved by techniques generally known in the art. Such techniques for forming solid formulations include spray-drying, evaporation, centrifugation, tangential flow filtration, and microfiltration. Drying equipment that may be used include, without limit, a spray dryer, a convection oven, microwave dryer, Buflowvac, freeze drying, or a rotary drum dryer. Powdered formulations may be prepared to include a bulking agent such as maltodextrin, corn starch, tapioca starch, tapioca dextrose, microcrystalline cellulose, rice flour, rice starch, a prebiotic such as inulin and fos.

In some embodiments, the liquid composition may be concentrated to form a more concentrated liquid composition. The liquid compositions may be concentrated using techniques generally known in the art. In some embodiments, more concentrated liquid composition may be prepared by centrifugation, ultra filtration, and evaporation.

In some embodiments, the solid compositions may be powdered or pelletized. The solid compositions may be powdered or pelletized using techniques generally known in the art.

In some embodiments, a formulation can be prepared to obtain a specific microbial count. In some embodiments, the formulation may contain a lactic acid bacterial count of at least about $1.0 \times 10^5$ cfu/gram or cfu/ml. In other embodiments, the formulation may contain a lactic acid bacterial count of at least $1.0 \times 10^7$ cfu/gram or cfu/ml. Typical lactic acid bacterial counts range from $1.0 \times 10^5$ to $1.0 \times 10^{10}$ cfu/gram or cfu/ml.

II. Methods

In an aspect, a method of the disclosure comprises treating or preventing a disease or condition in an animal in need thereof, the method comprising administering to the animal a composition comprising at least two microbes selected from the group consisting of *Lactobacillus reuteri*, *Pediococcus acidilactici*, and *Enterococcus faecium*, and optionally one or more of *Pediococcus pentosaceus*, *Lactobacillus acidophilus*, *Lactobacillus fermentum* and *Lactobacillus plantarum*, including any of the microbe compositions described in more detail above, together with the metabolites produced by the at least two microbes grown together in any of the media above, including any of the compositions described in more detail above.

In certain embodiments, methods of the disclosure comprise treating or preventing a disease or condition in an animal in need thereof, the method comprising administering to the animal a composition that comprises *Lactobacillus reuteri* and *Pediococcus acidilactici Lactobacillus reuteri*, *Pediococcus acidilactici*, and *Enterococcus faecium*; *Lactobacillus reuteri*, *Pediococcus acidilactici*, *Enterococcus faecium* and *Pediococcus pentosaceus*; or *Lactobacillus reuteri*, *Pediococcus acidilactici*, *Enterococcus faecium* and *Lactobacillus acidophilus* and the metabolites produced by the microbes when grown together in any of the media described above.

In an embodiment, the disease or condition may be a gastrointestinal disease. In a further embodiment, the disease or condition may affect a portion of the gastrointestinal tract. In an embodiment, the disease or condition may affect the duodenal portion of the gastrointestinal tract. In another embodiment, the disease or condition may affect the jejunal portion of the gastrointestinal tract.

In an embodiment, the disease or condition may be necrotic enteritis, *Salmonella* enteritis, coccidiosis, mastitis, Avian influenza, Fowl pox, infectious bronchitis, Quail bronchitis, Larygotracheitis, Newcastle Disease, mycotoxin poisoning, Porcine Sarcoptic Mange, Pleuropneumonia, gastric ulcers, intestinal torsion, Glasser's Disease, porcine parvovirus, vomiting and wasting disease, porcine epidemic diarrhea, bovine respiratory disease complex, Clostridial disease, bovine respiratory syncytial, bovine viral diarrhea, *Haemophilus somnus*, infectious bovine Rhinotracheitis, *Parinflenza type* 3, Pasteurella Haemolytical, or Pasteurella Multocida. In a further embodiment, the disease or condition may be necrotic enteritis, *Salmonella* enteritis, or coccidiosis mastitis.

In an embodiment, the disease or condition may be a fertility disease or condition. For example, administration of a formulation of the invention to an animal may increase the egg laying frequency of poultry, may reduce the incidence of stillborn or mummy births in mammal production animals and/or may increase the number of live births in mammal production animals.

In an embodiment, the disease or condition may be caused by an infectious microbial agent. In some embodiments, the infectious microbial agent may be a *Clostridium* species. The *Clostridium* species may be, without limit, *Clostridium absonum*, *Clostridium aceticum*, *Clostridium acetireducens*, *Clostridium acetobutylicum*, *Clostridium acidisoli*, *Clostridium aciditolerans*, *Clostridium acidurici*, *Clostridium aerotolerans*, *Clostridium aestuarii*, *Clostridium akagii*, *Clostridium aldenense*, *Clostridium aldrichii*, *Clostridium algidicarnis*, *Clostridium algidixy-*

*lanolyticum, Clostridium algifaecis, Clostridium algoriphilum, Clostridium alkalicellulosi, Clostridium amazonense, Clostridium aminophilum, Clostridium aminovalericum, Clostridium amygdalinum, Clostridium amylolyticum, Clostridium arbusti, Clostridium arcticum, Clostridium argentinense, Clostridium asparagiforme, Clostridium aurantibutyricum, Clostridium autoethanogenum, Clostridium baratii, Clostridium barkeri, Clostridium bartlettii, Clostridium beijerinckii, Clostridium bifermentans, Clostridium bolteae, Clostridium bornimense, Clostridium botulinum, Clostridium bowmanii, Clostridium bryantii, Clostridium butyricum, Clostridium cadaveris, Clostridium caenicola, Clostridium caminithermale, Clostridium carboxidivorans, Clostridium carnis, Clostridium cavendishii, Clostridium celatum, Clostridium celerecrescens, Clostridium cellobioparum, Clostridium cellulofermentans, Clostridium cellulolyticum, Clostridium cellulosi, Clostridium cellulovorans, Clostridium chartatabidum, Clostridium chauvoei, Clostridium chromiireducens, Clostridium citroniae, Clostridium clariflavum, Clostridium clostridioforme, Clostridium coccoides, Clostridium cochlearium, Clostridium colletant, Clostridium cocleatum, Clostridium colicanis, Clostridium colinum, Clostridium collagenovorans, Clostridium cylindrosporum, Clostridium difficile, Clostridium diolis, Clostridium disporicum, Clostridium drakei, Clostridium durum, Clostridium estertheticum, Clostridium estertheticum estertheticum, Clostridium estertheticum laramiense, Clostridium fallax, Clostridium felsineum, Clostridium fervidum, Clostridium fimetarium, Clostridium formicaceticum, Clostridium frigidicarnis, Clostridium frigoris, Clostridium ganghwense, Clostridium gasigenes, Clostridium ghonii, Clostridium glycolicum, Clostridium glycyrrhizinilyticum, Clostridium grantii, Clostridium haemolyticum, Clostridium halophilum, Clostridium hastiforme, Clostridium hathewayi, Clostridium herbivorans, Clostridium hiranonis, Clostridium histolyticum, Clostridium homopropionicum, Clostridium huakuii, Clostridium hungatei, Clostridium hydrogeniformans, Clostridium hydroxybenzoicum, Clostridium hylemonae, Clostridium jeddahense, Clostridium jejuense, Clostridium indolis, Clostridium innocuum, Clostridium intestinale, Clostridium irregulare, Clostridium isatidis, Clostridium josui, Clostridium kluyveri, Clostridium lactatifermentans, Clostridium lacusfryxellense, Clostridium laramiense, Clostridium lavalense, Clostridium lentocellum, Clostridium lentoputrescens, Clostridium leptum, Clostridium limosum, Clostridium litorale, Clostridium liquoris, Clostridium lituseburense, Clostridium ljungdahlii, Clostridium lortetii, Clostridium lundense, Clostridium luticellarii, Clostridium magnum, Clostridium malenominatum, Clostridium mangenotii, Clostridium mayombei, Clostridium maximum, Clostridium methoxybenzovorans, Clostridium methylpentosum, Clostridium moniliforme, Clostridium neopropionicum, Clostridium nexile, Clostridium nitrophenolicum, Clostridium novyi, Clostridium oceanicum, Clostridium orbiscindens, Clostridium oroticum, Clostridium oryzae, Clostridium oxalicum, Clostridium papyrosolvens, Clostridium paradoxum, Clostridium paraperfringens (Alias: C. welchii), Clostridium paraputrificum, Clostridium pascui, Clostridium pasteurianum, Clostridium peptidivorans, Clostridium perenne, Clostridium perfringens, Clostridium pfennigii, Clostridium phytofermentans, Clostridium piliforme, Clostridium polysaccharolyticum, Clostridium polyendosporum, Clostridium populeti, Clostridium propionicum, Clostridium proteoclasticum, Clostridium proteolyticum, Clostridium psychrophilum, Clostridium puniceum, Clostridium punense, Clostridium purinilyticum, Clostridium putrefaciens, Clostridium putrificum, Clostridium quercicolum, Clostridium quinii, Clostridium ramosum, Clostridium rectum, Clostridium roseum, Clostridium saccharobutylicum, Clostridium saccharogumia, Clostridium saccharolyticum, Clostridium saccharoperbutylacetonicum, Clostridium sardiniense, Clostridium sartagoforme, Clostridium saudiense, Clostridium senegalense, Clostridium scatologenes, Clostridium schirmacherense, Clostridium scindens, Clostridium septicum, Clostridium sordellii, Clostridium sphenoides, Clostridium spiroforme, Clostridium sporogenes, Clostridium sporosphaeroides, Clostridium stercorarium, Clostridium stercorarium leptospartum, Clostridium stercorarium stercorarium, Clostridium stercorarium thermolacticum, Clostridium sticklandii, Clostridium stramini solvens, Clostridium subterminale, Clostridium sufflavum, Clostridium sulfidigenes, Clostridium swellfunianum, Clostridium symbiosum, Clostridium tagluense, Clostridium tarantellae, Clostridium tepidiprofundi, Clostridium termitidis, Clostridium tertium, Clostridium tetani, Clostridium tetanomorphum, Clostridium thermaceticum, Clostridium thermautotrophicum, Clostridium thermoalcaliphilum, Clostridium thermobutyricum, Clostridium thermocellum, Clostridium thermocopriae, Clostridium thermohydrosulfuricum, Clostridium thermolacticum, Clostridium thermopalmarium, Clostridium thermopapyrolyticum, Clostridium thermosaccharolyticum, Clostridium thermosuccinogenes, Clostridium thermosulfurigenes, Clostridium thiosulfatireducens, Clostridium tyrobutyricum, Clostridium uliginosum, Clostridium ultunense, Clostridium ventriculi, Clostridium villosum, Clostridium vincentii, Clostridium viride, Clostridium vulturis, Clostridium xylanolyticum,* or *Clostridium xylanovorans.* In a further embodiment, the *Clostridium* species may be *Clostridium perfringens.*

In an embodiment, the composition may reduce the amount of pathogens present in the animal's feces.

In an embodiment, the composition may reduce the ammonia content of the animal's feces.

In an embodiment, the composition may reduce the amount of methane produced and expelled by the animal either in respiratory action or in digestive gas release to the environment.

In an embodiment, the composition may effect the feed conversion rate positively.

In an embodiment, the composition may reduce animal mortality rate.

In an embodiment, the composition may increase the average daily weight gain.

In an embodiment, the composition may increase egg shell quality and egg weight.

In an embodiment, the composition may modulate the gastrointestinal microbiome of an animal. In another embodiment, the composition may modulate the gastrointestinal immune response of an animal. In other embodiments, the composition may modulate the phosphorylation of gastrointestinal proteins of an animal.

In some embodiments, the solid compositions may be added to a feed ration of the animal or provided to the animal as a supplement.

In an embodiment, the composition may be provided in a solid form and added to an animal feed ration. In some embodiments, the solid composition may be added to an animal feed ration in an amount of from about 0.1 kg/ton to about 2.0 kg/ton of feed. In other embodiments, the solid composition may be added to an animal feed ration in an amount of about 0.1 kg/ton, about 0.25 kg/ton, about 0.5 kg/ton, about 0.75 kg/ton, about 1.0 kg/ton, about 1.25 kg/ton, about 1.5 kg/ton, about 1.75 kg/ton, or about 2.0 kg/ton.

In some embodiments, the liquid compositions may be added to the drinking water supply of the animal.

In an embodiment, the composition may be provided in a liquid form and added to an animal's drinking water. In some embodiments, the liquid composition may be added to animal's drinking water in an amount of from about 0.1 mL/day/animal to about 10 mL/day/animal. In other embodiments, the liquid composition may be added to an animal's drinking water in an amount of about 0.1 mL/day, about 0.25 mL/day, about 0.5 mL/day, about 1.0 mL/day, about 1.25 mL/day, about 1.5 mL/day, about 1.75 mL/day, about 2.0 mL/day, about 2.25 mL/day, about 2.5 mL/day, about 2.75 mL/day, about 3.0 mL/day, about 3.25 mL/day, about 3.5 mL/day, about 3.75 mL/day, about 4.0 mL/day, about 4.25 mL/day, about 4.5 mL/day, about 4.75 mL/day, about 5.0 mL/day, about 6.25 mL/day, about 6.5 mL/day, about 6.75 mL/day, about 7.0 mL/day, about 7.25 mL/day, about 7.5 mL/day, about 7.75 mL/day, about 8.0 mL/day, about 8.25 mL/day, about 8.5 mL/day, about 8.75 mL/day, about 9.0 mL/day, about 9.25 mL/day, about 9.5 mL/day, about 9.75 mL/day, or about 10.0 mL/day.

In an embodiment, the composition may be provided in a liquid form and added to a chicken's drinking water. In some embodiments, the liquid composition may be added to a chicken's drinking water in an amount of from about 0.1 mL/day to about 2 mL/day/animal. In other embodiments, the liquid composition may be added to a chicken's drinking water in an amount of about 0.1 mL/day/animal, about 0.25 mL/day/animal, about 0.5 mL/day/animal, about 1.0 mL/day/animal, about 1.25 mL/day/animal, about 1.5 mL/day/animal, about 1.75 mL/day/animal, or about 2.0 mL/day/animal.

In an embodiment, the composition may be provided in a liquid form and added to a pig's drinking water. In some embodiments, the liquid composition may be added to a pig's drinking water in an amount of from about 0.5 mL/day/animal to about 10 mL/day/animal. In other embodiments, the liquid composition may be added to a pig's drinking water in an amount of about 0.5 mL/day·animal, about 0.75 mL/day/animal, about 1.0 mL/day/animal, about 1.25 mL/day/animal, about 1.5 mL/day/animal, about 1.75 mL/day/animal, about 2.0 mL/day/animal, about 2.25 mL/day/animal, about 2.5 mL/day/animal, about 2.75 mL/day/animal, about 3.0, mL/day/animal, about 3.25 mL/day/animal, about 3.5 mL/day/animal, about 3.75 mL/day/animal, about 4.0 mL/day/animal, about 4.25 mL/day/animal, about 4.5 mL/day/animal, about 4.75 mL/day/animal, about 5.0 mL/day/animal, about 5.25 mL/day/animal, about 5.5 mL/day/animal, about 5.75 mL/day/animal, about 6.0 mL/day/animal, about 6.25 mL/day/animal, about 6.5 mL/day/animal, about 6.75 mL/day/animal, about 7.0 mL/day/animal, about 7.25 mL/day/animal, about 7.5 mL/day/animal, about 7.75 mL/day/animal, about 8.0 mL/day/animal, about 8.25 mL/day/animal, about 8.5 mL/day/animal, about 8.75 mL/day/animal, about 9.0 mL/day/animal, 9.25 mL/day/animal, about 9.50 mL/day/animal, about 9.75 mL/day/animal or about 10.0 mL/day/animal Those of skill in the art should, in light of the present disclosure, appreciate that many changes can be made in the specific embodiments which are disclosed and still obtain a like or similar result without departing from the spirit and scope of the invention.

Definitions

Bacterial species are presented herein by Latin names in accordance with the Linnaean taxonomic biological classification system. Accordingly, reference is made to microorganisms which can be with identified with reference to certain genus, species, subspecies and strain names.

The term "microbiome" as used herein, refers to the community of microbial species present in the gastrointestinal system of an animal.

The terms "probiotic" and "probiotic microorganism" as used herein, refers to a composition of one or more species of microorganisms which when orally administered can provide health benefits to an animal.

The term "prebiotic" as used herein, means a non-microbial ingredient for optional inclusion in a probiotic formulation capable of inducing growth or activity of probiotic microorganisms in the gastrointestinal system.

The term "postbiotic" as used herein, means a non-viable bacterial products or metabolic by products from probiotic microorganisms that have biologic activity in the host.

The terms "short chain fatty acids" or "SCFAs", as may be interchangeably used herein, include acetic acid, formic acid, propionic acid, butyric acid, isobutyric acid, valeric acid, succinic acid, and isovaleric acid.

As used herein, "animal" refers to, but are not limited to, a human, a livestock animal, a companion animal, a lab animal, and a zoological animal. In another embodiment, the animal may be a livestock animal. In an embodiment, the animal may be a bovine animal, a porcine animal, or a poultry animal. In other embodiments, the animal may be a cow, a pig, or a chicken. Non-limiting examples of suitable livestock animals may include pigs, cows, horses, goats, sheep, llamas, and alpacas. In yet another embodiment, the subject may be a companion animal. Non-limiting examples of companion animals may include pets such as dogs, cats, rabbits, and birds. In yet another embodiment, the animal may be a zoological animal. In an alternative embodiment, the animal may be a human.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Method of Procurement of Microorganisms for Use in a Fermentation Cocktail Formulation The strains used were single strain organism cultures stored in 15% to 25% glycerol:media. The strains were unique species obtained by the inventors from Pure Cultures, Inc., or obtained by bio prospecting from commercial dietary supplements or obtained from the USDA/NRRL culture bank.

Example 2

Method of Specimen Collection and Isolation of Bacteria from Feces

Fresh feces samples were gathered from healthy canine in Colorado, USA and immediately frozen at approximately −18° C. Fecal matter was added to peptone water (10% wt./vol.) and vortexed to fully homogenize samples. Serial dilutions of the fecal homogenate were then streaked onto MRS agar for isolation. Single colonies were selected, further purified via MRS agar isolation, and subsequently enriched in MRS broth once a pure colony was obtained. Enriched media was then diluted with 30% glycerol:water solution. 1 ml Aliquotes were then placed in 2 ml cryo vials and stored at −80° C.

Example 3

Method of Specimen Collection and Isolation of Bacteria from Commercial Dietary Supplement Product Purchased probiotic product was inoculated into to non-animal MRS media. Inoculated media was incubated at 37° for approximately 15 hours. A sterile inoculation loop was dipped into the media with growth and streaked on to a non-animal MRS agar plate. Plate was incubated overnight approximately 18 hours. Single colony was picked and placed in autoclaved non-animal media and incubated at 37° C. Enriched media was then diluted 1:1 with 50% glycerol:water solution. 1 ml Aliquotes were then placed in 2 ml cryo vials and stored at −80° C.

Example 4

Method of 16sRNA Sequencing for Identification of Strains

Strains were sent to MIDI Laboratories Newark, DE 19713. Approximately 500 base pairs were sequenced and compared to D16M3 Library Revision 3.01.

Example 5

Method of Full Genomic Sequencing of Bacterial Strains

Each strain was processed according to established SOPs at the ATCC-CTM. Genomic DNA was extracted from each strain using a QIAmp DNA Mini Kit (Qiagen Cat No./ID 51304) and subsequently quantified fluorometrically using a QUBIT 2.0 fluorometer as per the manufacturer's instructions (ThermoFisher Scientific).

The workflow for whole genome sequencing was conducted as recommended by Illumina. Library preparation was performed using the Nextera XT DNA Library Prep Kit (Illumina Cat No. FC-131-1096) as per manufacturer's instructions. Once the library was prepared and quality controlled—it was then sequenced using an Illumina MiSeq with the MiSeq Reagent Kit V3 600 cycles (Illumina Cat No. MS-102-3003). The resulting sequences were evaluated for read quality and accuracy using the application software FASTQC from Babrahm Bioinformatics, Babraham Institute, Cambridge, UK (<https://www.biinformatics.babraham.ac.uk/projects/fastqc/>). The QC'd, filtered sequences were then assembled into contigs and annotated using ATCC-CTM's proprietary Advanced Microbial Genomics (AMG) Platform.

Example 6

Method for Assaying SCFAs

A HPLC method using Agilent 1100 series HPLC unit. A Bio-Rad Organic Acid Analysis Column Aminex HPX-87H Ion Exclusion Column with 0.2 N H2SO4 stationary mobile phase. Heated to 60° C.

Diet based cross-feeding mechanism, as shown in FIG. 1, is a key feature in the mammalian, avian and reptilian gut microbiome. In order to understand the cross feeding mechanism, further modeling was conducted and compared to the whole genome metabolic models (of the same four strains) against several key SCFAs producers (reference gut microbiome species). Along with our four whole genome metabolic models the final cross feeding model was constructed using Bacteroides_thetaiotaomicron, Escherichia_coli_str_K_12, Clostridium_ramosum_VPI, Lactobacillus_plantarum. Cross feeding model was run on two key SCFAs (e.g. butyrate) producing metabolites i.e. lactate (secondary) and xylan (primary). Interestingly, all four strains showed significant cross feeding interactions with other reference strains. This result highlights the fact that the strains have the genetic/metabolic potential to efficiently produce the SCFAs using primary (xylan) and secondary (lactate) metabolic precursors for SCFAs production.

Example 7

Method for Evaluating Pathogen Inhibition

Antimicrobial activities of the LAB strains were tested with well diffusion assay using TSB agar plates. Known pathogen standard was inoculated overnight in TSB and incubated 37° C. for 24 hours+/−4 hours. 100 μL were spread on the TSB agar plate. Holes were punched in the agar and 25 μL of overnight ferment broth was inoculated into the well and allowed to incubate overnight at 37° C. The size of the inhibition halo is measured in mL. The results for certain strains are shown in the following table.

TABLE 5

E. coli inhibition of strains with different media

| Strain | media | agar | Lab notebook ref. | Well diffusion (mm) |
|---|---|---|---|---|
| Lactobacillus acidophilus PCLA18 | A | TSB | SKK1016p.006 | 14 |
| Lactobacillus reuteri R4 | A | TSB | SKK1016p.006 | 11 |
| Lactobacillus reuteri PCR7 PCR7 | A | TSB | SKK1016p006 | 18 |
| Lactobacillus reuteri LR2 commercially available strain | A | TSB | SKK1016p.006 | 12 |
| Lactobacillus acidophilus PCLA18 | B | TSB | SKK1016p.006 | 15 |
| Lactobacillus reuteri PCR4 | B | TSB | SKK1016p.006 | 15 |
| Lactobacillus reuteri PCR7 | B | TSB | SKK1016p.006 | 18 |

TABLE 5-continued

E. coli inhibition of strains with different media

| Strain | media | agar | Lab notebook ref. | Well diffusion (mm) |
|---|---|---|---|---|
| Lactobacillus reuteri LR2 commercially available strain | B | TSB | SKK1016p.006 | 15 |

Example 8

Method for BLASTing Sequence Data Against Known Databases

As shown in FIG. 3, draft genomes were annotated (Pathway and Enzyme level) using Prokka pipeline (<https://github.com/tseemann/prokka>). Taxonomic status was assigned to each genome using 400 marker gene dataset and finally compared against the reference genomes. A maximum likelihood tree was constructed (bootstrap=1000) with all four draft genomes and their top 50 closest phylogenetic neighbors.

Whole genome based phylogenetic analysis (above mentioned) clearly established the species level identity for each genome. The strain level identity of each genome was analyzed using pairwise whole genome average nucleotide identity (ANI) analysis with an established strain level cut-off of 99.9%. Pairwise ANI calculations clearly highlighted that all four strains i.e. L. reuteri PCR7, P. acidilactici PCLL01, E. faecium PCEF02, and L. fermentum PCF1 are novel strains in comparison to their closest species level genotype.

Using simulated micobiome data (from customized genome dataset of SCFA producing genomes) In situ replication rates were predicted across each genome using iRep tool (<https://github.com/christophertbrown/iRep>). Downstream analysis of in situ replication rates clearly highlighted the fast in situ growth in a gut environment (simulated using >500 cultured reference species genomes). Biopieces were used to extract the near complete sequences of the protein coding genes for mucus- and fibronectin-binding factors, implicated in adhesion to intestinal cells. Interestingly, L. fermentum PCF1 and L. reuteri PCR7 showed positive hit (BLASTx, e-value=10-e5) for mucin and fibronectin-binding proteins. Using Abricate (<https://github.com/tseemann/abricate>) pipeline, the draft genome assemblies were further screened for any ARG genes present in the close proximity of transposons and/or Integrons. As expected for a probiotic strain, none of the four draft genome showed any ARG gene in the close proximity of a transposons and/or Integron. These results clearly highlight the minimal horizontal gene transfer potential of the strains. Virulence factors were annotated by searching the Subsystem Feature Counts of the RAST output for those factors identified in the Virulence, Disease and Defense subsystem. The presence of bacteriocins in the assembled sequences was determined by comprehensive searches of the BACTIBASE database (<http://bactibase.hammamilab.org/main.php>). BACTIBASE contains calculated or predicted physicochemical properties of 230 bacteriocins produced by both Gram-positive (206) and Gram-negative bacteria (19). The information in this database allows rapid prediction of structure/function relationships in addition to the target organisms of these peptides, which provides better exploitation of their biological activity in both the medical and food sectors. Each assembly was used individually as queries for the searches.

Example 9

Method for Evaluation of SCFAs with Gas Chromatography and a FID Detector

Figure 4:
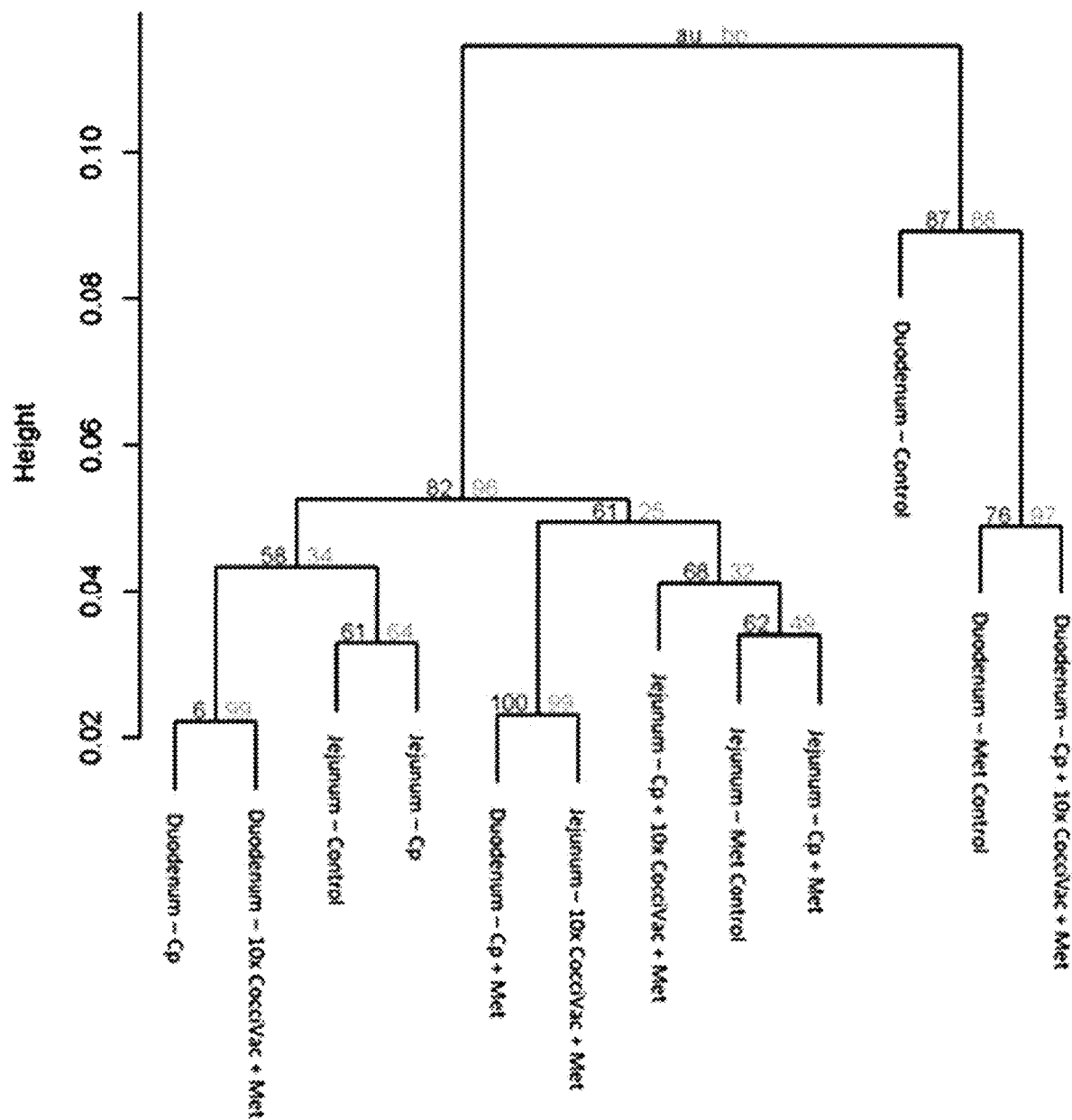
FIG. 4 is a diagram summarizing results obtained in the performance of an experiment, notably a heatmap and clustering of kinome profiles. The raw kinome signal from the peptide array was input into the custom software package PIIKA 2. PIIKA 2 combines the biological replicates for each treatment and tissue, normalizes the data, and generates a representative kinome profile. The profiles are compared for relative similarity and a heatmap shows the relative phosphorylation of each peptide on the array.
Figure 5:
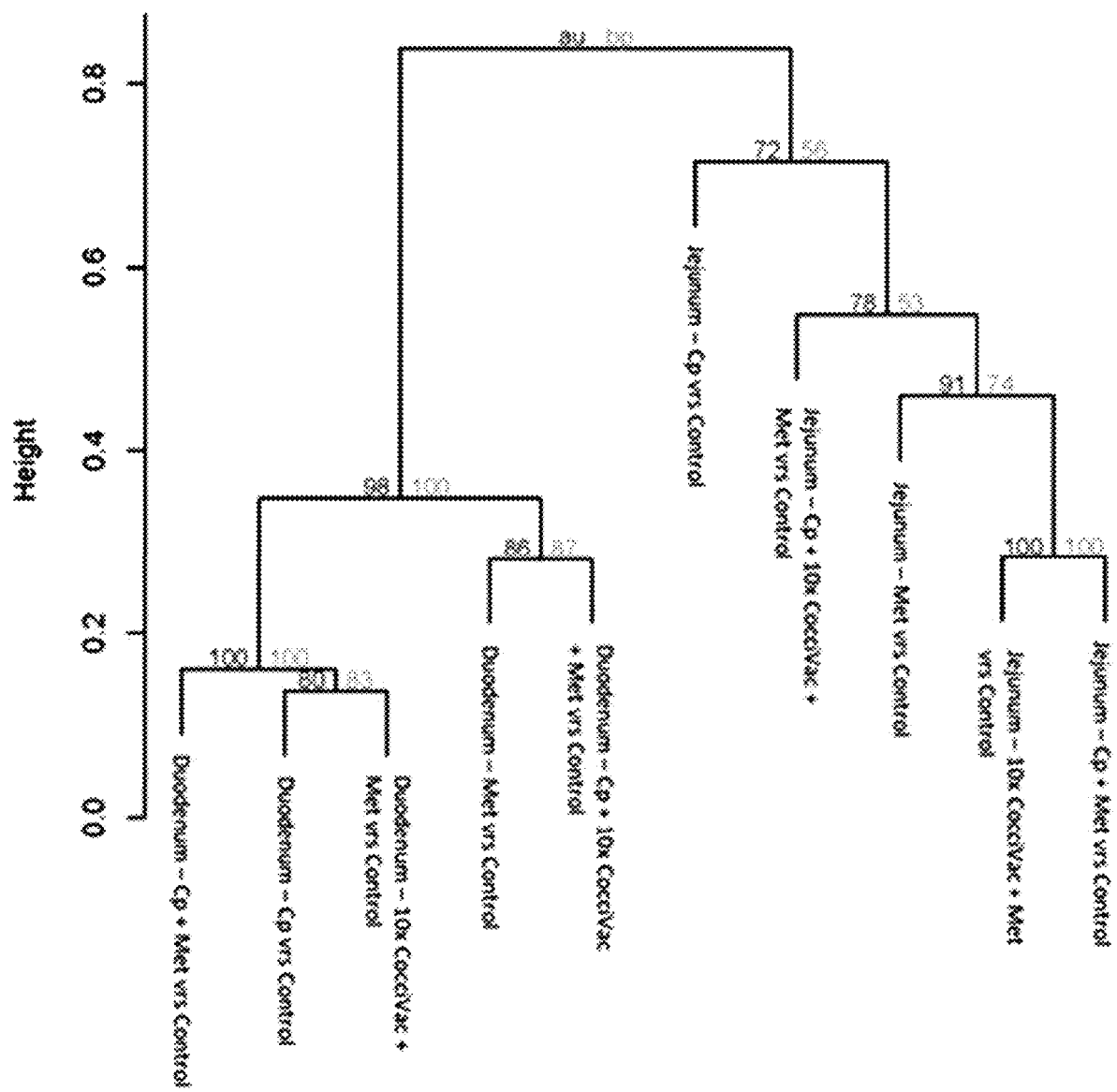
FIG. 5 is a diagram summarizing results obtained in the performance of an experiment, notably a BioSub Heatmap and clustering of treatment kinome profiles relative to control kinome profiles. The raw kinome signal from the peptide array was input into the custom software package PIIKA 2. PIIKA 2 combines the biological replicates for each treatment and tissue, normalizes the data, and generates a representative kinome profile. The profiles for each treatment group are compared to the kinome profile of control groups. The resulting kinome profiles are then compared for relative similarity and a heatmap shows the relative phosphorylation of each peptide on the array for a given treatment group relative to control.

Sample extracts were analyzed on an Agilent 6890 Series Gas Chromatograph equipped with flame ionization detection (GC-FID; Agilent Inc., Santa Clara, Calif.). Injection rate was 10:1 split ratio, and inlet temperature was 22° C. and translet line temperature was held at 230° C. Separation was achieved on a 30 m TG-WAX-A column (ThermoScientific, 0.25 mm ID, 0.25 um film thickness) at 100° C. for 1 minute and ramp rate of 8° C. per minute to 180° C., held at 180° C. for 1 minute, ramped to 200° C. at 20° C./min and held for 5 minutes. Helium carrier flow was maintained at 1.2 mL per minute. Short chain fatty acids were quantified using 5-point standard curves of commercially purchased standards (Sigma, St. Louis, Mo., USA) and normalized to internal standard signal. As shown in FIG. 4, acetic acid has a retention time of 5.4 and 5.5 minutes. Propionic acid has a retention time of 6.5 minutes. Butyric acid has a retention time of 7.7 minutes. Lactic acid has a retention time of 13.2 and 14.78 minutes, whereas ascorbic acid has retention times of 14.04 and 15.09 minutes.

Example 10

Method for Evaluation of Genome Assemblies Using Prokka Pipeline

Raw genomic sequences were assembled into contents using IDBA assembler, a novo assembler for single-cell and metagenomic sequencing. Contigs were annotated using UniProt database. Annotated results were parsed using BioPython GenBank. Using custom BASH and Python scripts the annotated files were parsed into enzyme and pathway level functional matrices, as shown in the table below.

TABLE 6

Heat Stabilized proteins

| Name of Heat Stable Protein | PCLF1 | PCEF02 | PCLL01 | PCR7 |
|---|---|---|---|---|
| 18 kDa heat shock protein | 0 | 1 | 0 | 0 |
| Heat shock protein 15 | 1 | 1 | 0 | 1 |
| Heat-inducible transcription repressor HrcA | 1 | 1 | 1 | 1 |
| Chaperone protein CipB | 0 | 1 | 1 | 0 |
| Chaperone protein DnaJ | 1 | 2 | 1 | 1 |
| Chaperone protein DnaK | 1 | 1 | 1 | 1 |
| Molecular chaperone Hsp31 and glyoxalase | 0 | 2 | 1 | 0 |

Table lists the number of copies present in the genome.

Example 11

Probiotic Formulation

Strains of the following microorganisms were obtained: Lactobacillus acidophilus PCLA18, Lactobacillus reuteri, strain PCR7, Pediococcus acidilacti, strain PCLL01, and Enterococcus faecium PCEF02 were combined and grown in a liquid growth medium comprising approximately 5% molasses, 5% inulin and 2.5% v/v glycerol. Upon completion of growth the medium together with the bacteria was harvested. The harvested material can be used as a probiotic.

Example 12

Phosphorylation of Duodenal and Jejunal Proteins by a Probiotic Formulation

Figure 6:
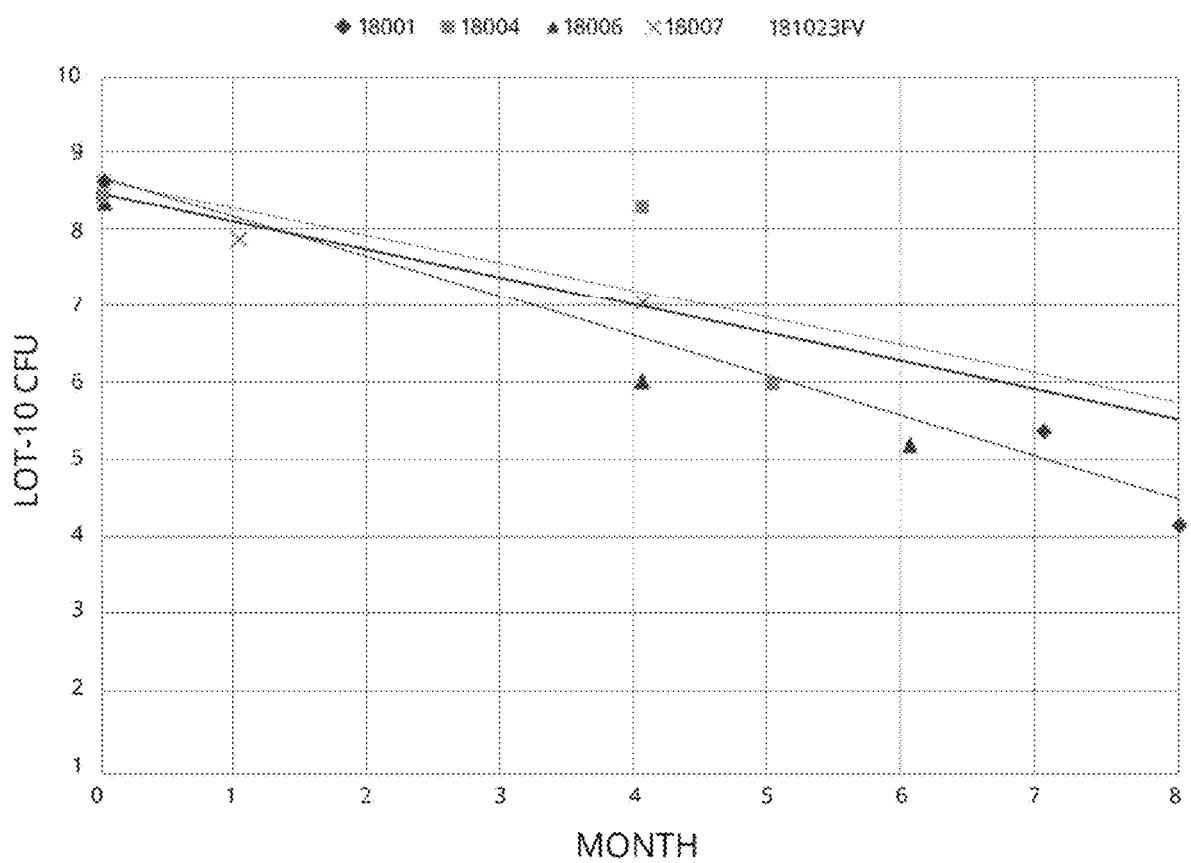
FIG. 6 is an enumeration graph by month.

A probiotic formulation was prepared as described in Example 11 and used in chicken feeding experiments. The duodenal and jejunal portions of the digestive tract kinome (Manning et al., 2002) of the chickens were evaluated. The following groups of chickens were evaluated: untreated control (group (i)); chickens treated the probiotic formulation (group (ii)); chickens challenged with *Clostridium perfringens* (group (iii)); chickens challenged with *Clostridium perfringens* and treated with the probiotic formulation (group (iv)); chickens treated with a Coccidiosis vaccine and probiotic formulation (group (v)); and chickens with *Clostridium perfringens* and treated with a Coccidiosis vaccine and probiotic formulation (group (vi)). Biological replicate samples from 5 birds per group were combined to generate representative kinome profiles. Following data combination and normalization, cluster analysis was performed on the resulting 12 kinome profiles (one for each tissue (jejunum and duodenum) (2) X treatment group ((i)-(vi)) (6)) using the custom software package PIIKA 2 (Trost et al., 2013). FIG. 6 shows a heatmap and clustering displaying the relative similarity between the 12 profiles based on phosphorylation of individual proteins. A further heat map was created representing the kinome profiles of the treatment/tissue combinations relative to the control kinome profiles for each respective tissue, as show in FIG. 7.

An effect of the probiotic formulation can be seen in FIG. 6. Jejunum tissue obtained from chickens treated with the probiotic formulation tend to cluster together. Duodenum tissue samples do not seem to develop a particular clustering pattern. Jejunum tissue samples obtained from chickens not treated with the probiotic formulation also form a cluster. This suggests that the probiotic treatment has a distinct effect on jejunal tissue, separate from the effect of the *Clostridium perfringens* challenge Referring to FIG. 7, duodenum tissue samples again shows little differentiation between groups. Jejunum tissue samples again seem to cluster based on metabolite treatment with the non-probiotic formulation treated group standing separate. The most removed from the metabolite cluster is the *Clostridium perfringens* induced necrotic enteritis probiotic treated group, suggesting the greatest changes occurring in this group relative to control when compared to the other metabolite treated groups.

Example 13

Identification of Jejunal Biological Processes and Signaling Pathways Following Treatment with a Probiotic Formulation In a peptide array obtained from the groups of chickens (i)-(iv) described in Example 12, individual peptides exhibiting differential phosphorylation patterns in jejunal tissue samples, relative to untreated control chickens (i) were identified. These individual were subjected to a protein STRING analysis (Szklarczyk D et al., 2015; <https://string-db.org>) to reveal relevant biological processes (GO), and a KEGG analysis (Kanesha M, Goto S, 2000; <https://www.genome.jp/kegg/pathway.html>) to reveal relevant signaling pathways. Table 7 and Table 8 show the STRING and KEGG results obtained using probiotic treated chickens (group (ii)); Table 9 and Table 10 show the STRING and KEGG results obtained using *Clostridium perfringens* challenged chickens (group (iii)); and Table 11 and Table 12 show the STRING and KEGG results obtained using *Clostridium perfringens* challenged chickens treated with probiotic (group (iv)).

It is noted that some of the biological processes may overlap between the Tables, the members of the biological processes had to be unique in order to be included in the analysis. Therefore, the same terms may appear between groups, but they are being enriched in different ways between the groups. This indicates that the various biological processes enriched are behaving in different ways between the treatment groups.

Highlighted in Table 7 and Table 9 are the terms related to immune signaling. All of the biological processes highlighted in the probiotic groups (Table 7) also appear in the *Clostridium perfringens* challenge groups (Table 9), but it is important to note that the lists used to generate these tables were unique to each group. Thus, although the same terms appear, they represent changes in the same biological processes between the treatment groups. Interestingly, the Probiotic+*Clostridium perfringens* challenge group (Table 11) does not have the same immune related biological pathways enriched in the top 20 pathways from the STRING analysis. This shows that the overlap of the two treatments, probiotic and *Clostridium perfringens* challenge, likely are imparting their own unique effects in jejunal tissue, which, when brought together, do not enrich new immune related biological processes.

With respect to Table 8, Table 10, and Table 12, it is noted that the KEGG pathways may overlap between the Tables, the members of the pathways had to be unique in order to be included in the analysis, therefore, the same terms may appear between groups, but they are being enriched in different ways between the groups. This indicates that the various KEGG pathways enriched are behaving in different ways between the treatment groups.

TABLE 7

Top 20 Biological Processes (GO) enriched uniquely in jejunum tissue of probiotic treated chickens compared to untreated chickens

| Biological Process | # of proteins | false discovery rate |
| --- | --- | --- |
| cellular response to chemical stimulus | 36 | 8.62E−12 |
| cellular response to organic substance | 32 | 3.00E−11 |
| phosphorylation | 25 | 9.43E−11 |
| transmembrane receptor protein tyrosine kinase signaling pathway | 21 | 1.13E−10 |
| enzyme linked receptor protein signaling pathway | 23 | 2.10E−10 |
| protein phosphorylation | 21 | 1.03E−09 |
| regulation of signaling | 34 | 7.35E−09 |
| regulation of response to stimulus | 36 | 6.90E−08 |
| regulation of immune response | 19 | 6.90E−08 |
| phosphorus metabolic process | 27 | 7.12E−08 |
| response to organic substance | 31 | 7.12E−08 |
| regulation of cell communication | 33 | 9.58E−08 |
| regulation of immune system process | 23 | 1.57E−07 |
| phosphate-containing compound metabolic process | 26 | 1.94E−07 |
| cell surface receptor signaling pathway | 27 | 6.22E−07 |
| regulation of signal transduction | 29 | 6.58E−07 |
| response to chemical | 36 | 9.23E−07 |
| positive regulation of immune system process | 17 | 2.70E−06 |

TABLE 7-continued

Top 20 Biological Processes (GO) enriched uniquely in jejunum tissue of probiotic treated chickens compared to untreated chickens

| Biological Process | # of proteins | false discovery rate |
|---|---|---|
| innate immune response | 18 | 2.70E−06 |
| single-organism metabolic process | 37 | 4.38E−06 |

TABLE 8

Top 20 KEGG pathways enriched uniquely in jejunum tissue of probiotic treated chickens compared to untreated chickens

| KEGG Pathway | # of proteins | false discovery rate |
|---|---|---|
| PI3K-Akt signaling pathway | 14 | 6.90E−09 |
| Fc gamma R-mediated phagocytosis | 9 | 6.90E−09 |
| Epstein-Barr virus infection | 11 | 1.56E−08 |
| Pancreatic cancer | 7 | 2.58E−07 |
| Non-alcoholic fatty liver disease (NAFLD) | 9 | 3.08E−07 |
| Ras signaling pathway | 10 | 4.99E−07 |
| Toxoplasmosis | 8 | 4.99E−07 |
| Influenza A | 9 | 5.57E−07 |
| Osteoclast differentiation | 8 | 7.90E−07 |
| Hepatitis C | 8 | 9.40E−07 |
| Measles | 8 | 9.40E−07 |
| Pathways in cancer | 11 | 9.70E−07 |
| Hepatitis B | 8 | 1.42E−06 |
| VEGF signaling pathway | 6 | 2.15E−06 |
| Toll-like receptor signaling pathway | 7 | 2.40E−06 |
| TNF signaling pathway | 7 | 3.14E−06 |
| Fc epsilon RI signaling pathway | 6 | 3.49E−06 |
| Adipocytokine signaling pathway | 6 | 3.61E−06 |
| Prolactin signaling pathway | 6 | 4.08E−06 |
| Adherens junction | 6 | 4.19E−06 |

TABLE 9

Top 20 Biological Processes (GO) enriched uniquely in jejunum tissue of Cp challenged chickens compared to unchallenged chickens

| Biological Process | # of proteins | false discovery rate |
|---|---|---|
| regulation of immune response | 20 | 3.90E−09 |
| protein metabolic process | 38 | 1.15E−08 |
| cellular protein metabolic process | 35 | 1.31E−08 |
| positive regulation of metabolic process | 35 | 1.80E−08 |
| regulation of phosphate metabolic process | 24 | 1.80E−08 |
| intracellular signal transduction | 26 | 1.80E−08 |
| defense response | 23 | 2.02E−08 |
| regulation of phosphorylation | 22 | 2.02E−08 |
| positive regulation of immune response | 16 | 2.02E−08 |
| immune response-regulating signaling pathway | 15 | 2.44E−08 |
| regulation of protein modification process | 24 | 2.47E−08 |
| protein phosphorylation | 18 | 3.17E−08 |
| innate immune response | 19 | 3.93E−08 |
| regulation of immune system process | 22 | 4.69E−08 |
| activation of immune response | 14 | 5.11E−08 |
| response to nitrogen compound | 18 | 8.11E−08 |
| immune response-activating signal transduction | 13 | 1.35E−07 |
| Fc receptor signaling pathway | 11 | 1.35E−07 |
| Fc-epsilon receptor signaling pathway | 10 | 1.46E−07 |
| regulation of protein phosphorylation | 20 | 1.60E−07 |

TABLE 10

Top 20 KEGG pathways enriched uniquely in jejunum tissue of Cp challenged chickens compared to unchallenged chickens

| KEGG Pathway | # of peptides | false discovery rate |
|---|---|---|
| Insulin signaling pathway | 8 | 4.18E−06 |
| T cell receptor signaling pathway | 7 | 5.66E−06 |
| Neurotrophin signaling pathway | 7 | 1.14E−05 |
| Natural killer cell mediated cytotoxicity | 7 | 1.36E−05 |
| Focal adhesion | 8 | 2.00E−05 |
| Prostate cancer | 6 | 2.00E−05 |
| Estrogen signaling pathway | 6 | 2.93E−05 |
| Pathways in cancer | 9 | 4.47E−05 |
| Glioma | 5 | 6.17E−05 |
| Fc epsilon RI signaling pathway | 5 | 8.24E−05 |
| Osteoclast differentiation | 6 | 8.79E−05 |
| Prolactin signaling pathway | 5 | 8.79E−05 |
| Hepatitis C | 6 | 0.000102 |
| ErbB signaling pathway | 5 | 0.000183 |
| MAPK signaling pathway | 7 | 0.000416 |
| Endometrial cancer | 4 | 0.000436 |
| Viral carcinogenesis | 6 | 0.000532 |
| Non-small cell lung cancer | 4 | 0.000532 |
| FoxO signaling pathway | 5 | 0.000803 |
| Measles | 5 | 0.00108 |

TABLE 11

Top 20 Biological Processes (GO) enriched uniquely in jejunum tissue of Cp challenged chickens treated with probiotic compared to non-challenged untreated chickens

| Biological Process | # of proteins | false discovery rate |
|---|---|---|
| protein autophosphorylation | 11 | 9.87E−09 |
| enzyme linked receptor protein signaling pathway | 17 | 5.74E−08 |
| transmembrane receptor protein tyrosine kinase signaling pathway | 15 | 1.05E−07 |
| regulation of cellular protein metabolic process | 21 | 1.08E−05 |
| regulation of intracellular signal transduction | 17 | 1.08E−05 |
| positive regulation of kinase activity | 11 | 1.18E−05 |
| positive regulation of lipid metabolic process | 7 | 1.18E−05 |
| intracellular signal transduction | 18 | 4.55E−05 |
| regulation of protein kinase activity | 12 | 4.55E−05 |
| response to external stimulus | 18 | 4.88E−05 |
| positive regulation of catalytic activity | 16 | 4.88E−05 |
| regulation of multicellular organismal process | 20 | 4.88E−05 |
| positive regulation of molecular function | 17 | 6.06E−05 |
| peptidyl-tyrosine phosphorylation | 7 | 6.85E−05 |
| protein phosphorylation | 12 | 0.000123 |
| regulation of cellular component biogenesis | 11 | 0.000123 |
| regulation of protein modification process | 16 | 0.000124 |
| regulation of protein phosphorylation | 14 | 0.000128 |
| positive regulation of intracellular signal transduction | 12 | 0.000132 |
| axon guidance | 9 | 0.000151 |

TABLE 12

Top 20 KEGG pathways enriched uniquely in jejunum tissue of Cp challenged chickens treated with probiotic compared to non-challenged untreated chickens

| KEGG Pathway | # of proteins | false discovery rate |
|---|---|---|
| AMPK signaling pathway | 7 | 4.40E−06 |
| Acute myeloid leukemia | 5 | 3.23E−05 |
| Chemokine signaling pathway | 6 | 0.000441 |
| Insulin signaling pathway | 5 | 0.00125 |

TABLE 12-continued

Top 20 KEGG pathways enriched uniquely in jejunum
tissue of Cp challenged chickens treated with probiotic
compared to non-challenged untreated chickens

| KEGG Pathway | # of proteins | false discovery rate |
|---|---|---|
| PI3K-Akt signaling pathway | 6 | 0.00685 |
| Leukocyte transendothelial migration | 4 | 0.00685 |
| Pathways in cancer | 6 | 0.00685 |
| mTOR signaling pathway | 3 | 0.0146 |
| ErbB signaling pathway | 3 | 0.0329 |
| Endocytosis | 4 | 0.0329 |
| Fc gamma R-mediated phagocytosis | 3 | 0.0329 |
| Regulation of actin cytoskeleton | 4 | 0.0397 |
| Proteoglycans in cancer | 4 | 0.0405 |
| Thyroid cancer | 2 | 0.0405 |

Example 14

Evaluation of Animal Health Parameters Following Treatment with a Probiotic Formulation A probiotic formulation was prepared as described in Example 11 and used in chicken feeding experiments. Various animal health parameters were evaluated. The following groups of chickens were evaluated: untreated control (T1); chickens treated the probiotic formulation (T2); chickens challenged with a coccidiosis vaccine (T3); chickens challenged with *Clostridium perfringens* and treated with a coccidiosis vaccine (T4); chickens challenged with *Clostridium perfringens* (T5); chickens challenged with *Clostridium perfringens* and treated with probiotic formulation (T6); chickens treated a coccidiosis vaccine and with probiotic formulation (T7); and chickens challenged with *Clostridium perfringens* and treated with a coccidiosis vaccine and a probiotic formulation (T8). The following health parameters were evaluated: (a) colony forming units of *Clostridium perfringens* in the intestine; (b) body weight gain; (c) *Clostridium perfringens* induced necrotic enteritis lesions; and (d) mortality. The experimental design is further summarized in Table 13.

Example 15

Producing and Detecting a Unique Blend of Organic Acids in a Consortium Liquid Cocktail for Poultry Health Introduction. Lactic acid bacteria (Lactobacilli) have been studied for decades, and one well-known function of these organisms is their ability to metabolize short-chain organic acids from 5- and 6-carbon sugar sources (Urdaneta, et al., 1995). Examples of such acids include acetic, butyric, formic, lactic, and propionic (Zalán, Hudáček, Štětina, Chumchalová, & Halász, 2009).

Methods. All techniques were performed aseptically. For each fermentation trial, up to four individual Lactobacilli strains were chosen from 15%-25% glycerol/MRS freezer stocks. They were subsequently incubated for 1 to 2 days at to 37° C.+/−2° C. Following this initial propagation, all of the strains were combined in pasteurized media and deionized water and incubated for 5 to 15 days at 30 to 37° C.+/−2° C. The resulting samples were individually resolved by HPLC, utilizing AOAC 986.13 (mod). Analysis was performed with a refractive index detector, and peaks were identified by comparison to organic acid standards.

Results. Small organic acids are the end products of the fermentation of a chosen carbon (sugar) source by a chosen combination of *Lactobacilli*. The selection of a particular carbon source and microorganism combination may result in the production of three main organic acids, as is displayed in Table 14 and Table 15.

TABLE 14

| Organic acid production | | |
|---|---|---|
| Single Organism in molasses media | Major Peaks not (lactic and acetic acid) | Lactic acid and acetic acid |
| PCLL01 *Pediococcus acidilactici* | 3, 4, 5 area ratios 3:1:2 | Lactic acid 7,000 ppm Acetic acid 1,000 ppm |
| PCEF02 *Enterococcus faecium* | 3, 5 no peak 4 ratio 1:5 | Lactic acid 10,000 ppm Acetic acid 3,000 ppm |

TABLE 13

| Experimental design | | | | | |
|---|---|---|---|---|---|
| Treatment | Groups | Body Weights | Coccidial Challenge | *Clostridium perfringens* | Lesion Score |
| T1* | Negative Control | Day 1, 14, 21 | No | No | Day 21 |
| T2* | Neg control + Probiotic | Day 1, 14, 21 | No | No | Day 21 |
| T3* | Cocci Vac | Day 1, 14, 21 | Day 14 | No | Day 21 |
| T4 | Cocci Vac + *Clostridium perfringens* | Day 1, 14, 21 | Day 14 | Day 17, 18, and 19* | Day 21 |
| T5 | Positive *Clostridium perfringens* control | Day 1, 14, 21 | No | Day 17, 18, and 19* | Day 21 |
| T6 | *Clostridium perfringens* + Probiotic | Day 1, 14, 21 | No | Day 17, 18, and 19* | Day 21 |
| T7* | Cocci Vac + Probiotic | Day 1, 14, 21 | Day 14 | No | Day 21 |
| T8 | CocciVac + *Clostridium perfringens* + Probiotic | Day 1, 14, 21 | No | Day 17, 18, and 19* | Day 21 |

The following results were obtained when comparing T8 with T4 and T5: (a) A significant reduction in total CFU of *Clostridium perfringens* in the intestine was observed (1.7 × 105 (T8) vs 6.2 × 105 (T4) and 14.0 × 105 (T5), respectively); (b) A significant larger body weight gain: (781 gram (T8) vs 697 gram (T4) and 695 gram (T5), respectively). As a comparison, T1 (negative control) had an average weight gain of 805 gram; (c) A significant reduction in lesion score: (0.56(T8) vs 2.3 (T4) and 3.0 (T5), respectively); and (d) A significant reduction in mortality: (1/50 (T8) vs 12/50 (T4) and 21/50 (T5), respectively).

TABLE 14-continued

Organic acid production

| Single Organism in molasses media | Major Peaks not (lactic and acetic acid) | Lactic acid and acetic acid |
|---|---|---|
| PCR7 Lactobacillus reuteri | Peak 3 and 5 No peak 4. Huge peak at 20.93 retention time | Lactic acid 7,000 ppm Acetic acid 2,000 ppm |
| PCPP01 Pediococus pentosaceus | 3, 4, 5 area ratios 3:1:2 | Lactic acid 9,000 ppm Acetic acid <1,000 ppm |

Multiple batches have been evaluated using the Pure Cultures in-house SOP SCFAHLC001 for purity and short chain fatty acid finger print. The first batch 17014 containing strains Lactobacillus reuteri PCR7, Pediococcus acidilactici PCLL01, Pediococcus pentosaceus PPPC01, and Enterococcus faecium PCEF01, produced for trial #1 at Texas A&M University was assayed after six months and in addition it was heated to 90° C. for 5 minutes. A second batch 18007, containing strains Lactobacillus fermentum PCLF01, Lactobacillus reuteri PCR7, Pediococcus acidilactici PCLL01, Pediococcus pentosaceus PCPP01, Enterococcus faecium PCEF02 was assayed using the same evaluation SOP for purity.

TABLE 15

Organic acid production

| Consortium product with 4 Organisms in molasses media | Major Peaks not (lactic and acetic acid) | Lactic acid and acetic acid |
|---|---|---|
| 17014 Original assay | 3, 4, 5 area ratios 1:1:1 | Lactic acid 3,000 ppm Acetic acid <1,000 ppm |
| 17014 heated to 90° C. | 3, 4, 5 area ratios 1:1:1 | Lactic acid 3,000 ppm Acetic acid <1,000 ppm |
| 17014 six month check | 3, 4, 5 area ratios 1:1:1 | Lactic acid 4,000 ppm Acetic acid 1,000 ppm |
| 18007 | 3, 4, 5 area ratios 1:1:1 | Lactic acid 4,000 ppm Acetic acid 2,000 ppm |

Discussion. The techniques described herein provide a quick and reliable method for the detection and initial characterization of organic acids produced in solution by fermentation. Providing evidence of a reproducible fermentation process and the ability to produce a unique and proprietary formulation. The careful selection of carbon sources and/or microorganisms can result in a controlled fermentation environment for the production of specific organic acids. As discussed in the Introduction, the selection of particular organic acids is important for both the weight-gain and anti-pathogen inhibition in poultry.

Example 16

Enumeration Tests

Based on USP<2021> Microbial Enumeration Tests for Dietary Supplements. Total Microbial Count plate method.

Samples are collected and shipped to third party laboratory. Samples are shipped overnight with ice packs to ensure stored <10° C.

Media Preparation:

Lactobacilli MRS agar+0.5 g/L-Cysteine is prepared per directions on package with the addition of L Cysteine. MRS media+0.5 g/L-Cysteine is prepared per directions on package with the addition of L Cysteine.

10.0 g of sample is aseptically weighed and diluted in 90 ml sterile buffered peptone. Sample and buffer are homogenized. 1 ml is removed and diluted with 99 ml peptone buffer to make −3 log dilution. Continue to serial dilute until 3 dilutions are made around the estimate of the final lactic acid bacteria count.

Inoculate 0.1 ml per plate of MRS agar+Cysteine. Spread with sterile spreader. Allow inoculum to absorb into the agar. Place in anaerobe chamber and incubate at 37° C. for 48 to 72 hours. After appropriate incubation time colonies are counted on agar plates with a target yield between 30-300 per plate. Results are shown in FIG. 6 and Table 16.

TABLE 16

Lactic acid bacteria enumeration of batches

| Batch # | Date of manufacture | Original LAB assay | 7.5 months @ room temperature | 8.3 months @ room temperature | Final Product specification 10M cfu/ml |
|---|---|---|---|---|---|
| 18001 | Feb. 1, 2018 | 430000000 cfu/ml | 300,000 cfu/ml | 20000 cfu/ml | 2.0 months ≥5.0 × 10^7 3.3 months ≥1.0 × 10^7 |

| Batch # | Date of manufacture | Original LAB assay | 3.9 months @ room temperature | 5.4 months @ room temperature | Final Product specification 10M cfu/ml |
|---|---|---|---|---|---|
| 18004 | Mar. 29, 2018 | 272,000,000 cfu/ml | 220,000,000 cfu/ml | 1,100,000 cfu/ml | 4.0 months ≥5.0 × 10^7 4.5 months ≥1.0 × 10^7 |

| Batch # | Date of manufacture | Original LAB assay | 3.9 months @ room temperature | 5.4 months @ room temperature | Final Product specification 10M cfu/ml |
|---|---|---|---|---|---|
| 18006 | May 19, 2018 | 245,000,000 cfu/ml | 1,200,000 cfu/ml | 200,000 cfu/ml | 1.5 months ≥5.0 × 10^7 2.5 months ≥1.0 × 10^7 |

TABLE 16-continued

Lactic acid bacteria enumeration of batches

| Batch # | Date of manufacture | Original LAB assay | 1.23 months @ room temperature | 4.1 months @ room temperature | Final Product specification 10M cfu/ml |
|---|---|---|---|---|---|
| 18007 | Aug. 25, 2018 | 420,000,000 cfu/ml | 81,000,000 cfu/ml | 13,000,000 cfu/ml | 2.2 months ≥5.0 × 10^7<br>4.0 months ≥1.0 × 10^7 |

| Batch # | Date of manufacture | Original LAB assay | 1.23 months @ room temperature | Final Product specification 10M cfu/ml |
|---|---|---|---|---|
| 181023FV | Oct. 25, 2018 | 1,100,000,000 cfu/ml | 190,000,000 cfu/ml | 1.8 months ≥5.0 × 10^7<br>2.6 months ≥1.0 × 10^7 |

Average 2.2 months @ ≥5.0 × 10^7;
Average 4.83 months @ ≥1.0 × 10^7

Batch 18001 contains strains *Lactobacillus fermentum* PCLF01, *Lactobacillus reuteri* PCR7, *Pediococcus acidilactici* PCLL01, *Pediococcus pentosaceus* PCPP01, *Enterococcus faecium* PCEF01

Batch 18004 contains strains *Lactobacillus fermentum* PCLF01, *Lactobacillus reuteri* PCR7, *Pediococcus acidilactici* PCLL01, *Pediococcus pentosaceus* PCPP01, *Enterococcus faecium* PCEF01

Batch 18006 contains strains *Lactobacillus fermentum* PCLF01, *Lactobacillus reuteri* PCR7, *Pediococcus acidilactici* PCLL01, *Pediococcus pentosaceus* PCPP01, *Enterococcus faecium* PCEF01

Batch 18007 contains strains *Lactobacillus fermentum* PCLF01, *Lactobacillus reuteri* PCR7, *Pediococcus acidilactici* PCLL01, *Pediococcus pentosaceus* PCPP01, *Enterococcus faecium* PCEF01

Batch 181023 contains strains *Lactobacillus reuteri* PCR7, *Pediococcus acidilactici* PCLL01, *Pediococcus pentosaceus* PCPP01, *Enterococcus faecium* PCEF01

Example 17

90° C. Stability Test

Formulation batch 17014 containing strains *Lactobacillus reuteri* PCR7, *Pediococcus acidilactici* PCLL01, *Pediococcus pentosaceus* PPPC01, and *Enterococcus faecium* PCEF01 in a molasses media was placed in a heating oven that at a temperature set point of 90° C. Approximately 10 mls of sample were heated to 90° C. in heating oven. A piece of aluminum foil was placed on top of the beaker while it was being heated. Once the sample reached 90° C. a timer was started. At 5 minutes sample was removed from the oven and placed in a refrigerator until temperature was approximately 40° C. Sample was sent to Midi Laboratories in Omaha, Neb. where Organic Acids were assayed using AOAC 986.13 (mod) assay.

A HPLC method using Agilent 1100 series HPLC unit. A Bio-Rad Organic Acid Analysis Column Aminex HPX-87H Ion Exclusion Column with 0.2 N H2SO4 stationary mobile phase.

Figure 7:
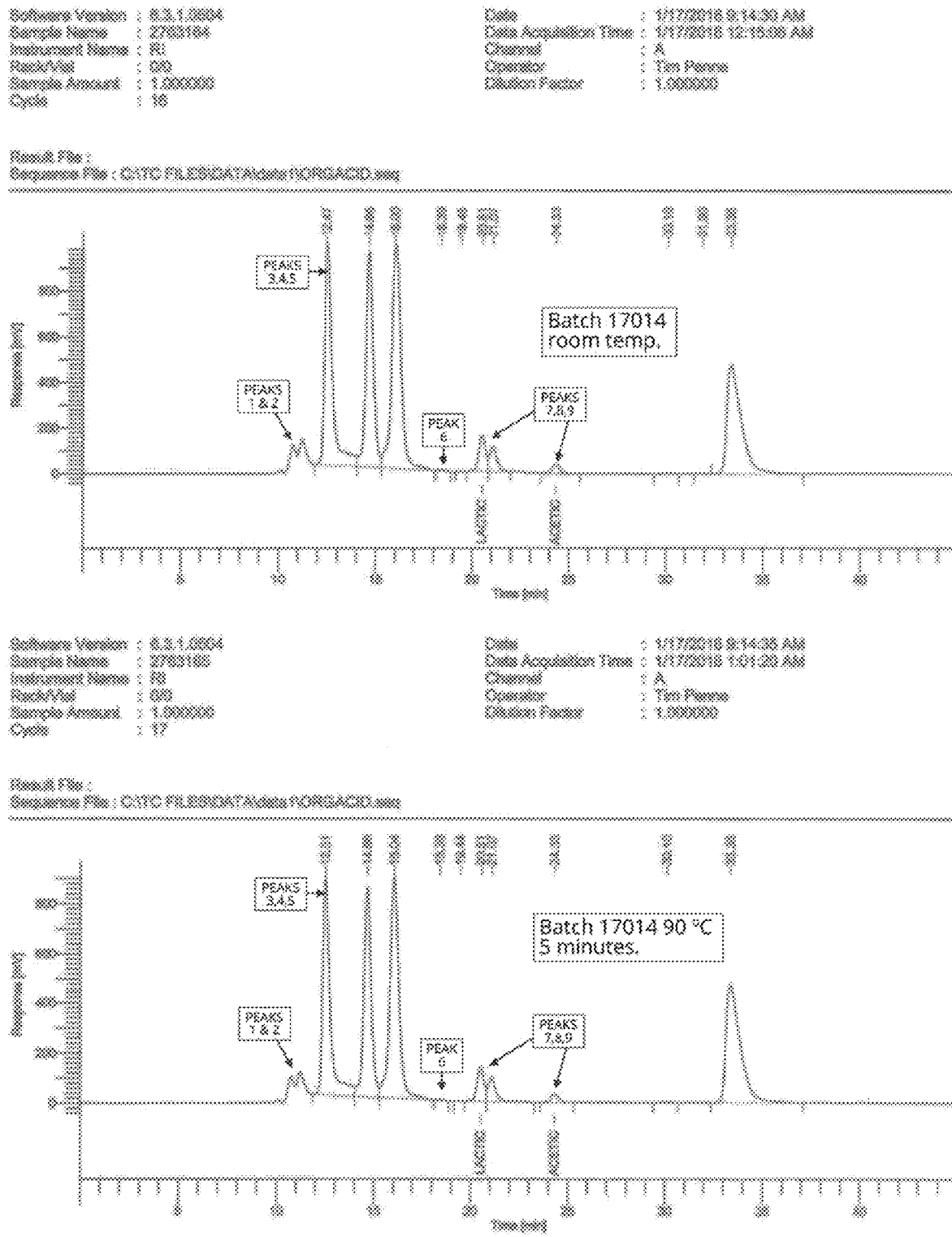
FIG. 7 presents data for 90° C. stability tests.

Organic acid chromatography was evaluated for similarities in peaks and areas of each peak present between a sample that was not heated and a sample that was heated to 90° C. Step 1. Determine that there are 9 peaks present in both chromatographs. If there is a new peak present in either sample ensure that its area is not >1.5% of all areas added together. Step 2. Ensure that the area of peaks 3,4 and 5 are in the ratio of 1:1:1. Step 3. Verify that the lactic acid and acetic acid concentrations in both samples are +/−0.5% of the concentration each sample. Results are shown in FIG. 7.

Example 18

Six Month Stability Test

Formulation batch 17014 containing strains *Lactobacillus reuteri* PCR7, *Lactobacillus fermentum* PCLF01, *Pediococcus acidilactici* PCLL01, *Pediococcus pentosaceus* PPPC01, and *Enterococcus faecium* PCEF01 in a molasses media was stored at room temperature approximately 22° C.+/−2° C. It was stored in an 8 ounce plastic HDPE bottle. After six months of storage a sample was sent to Midi Laboratories in Omaha, Neb. where Organic Acids were assayed using AOAC 986.13 (mod) assay.

A HPLC method using Agilent 1100 series HPLC unit. A Bio-Rad Organic Acid Analysis Column Aminex HPX-87H Ion Exclusion Column with 0.2 N H2SO4 stationary mobile phase.

Figure 8:
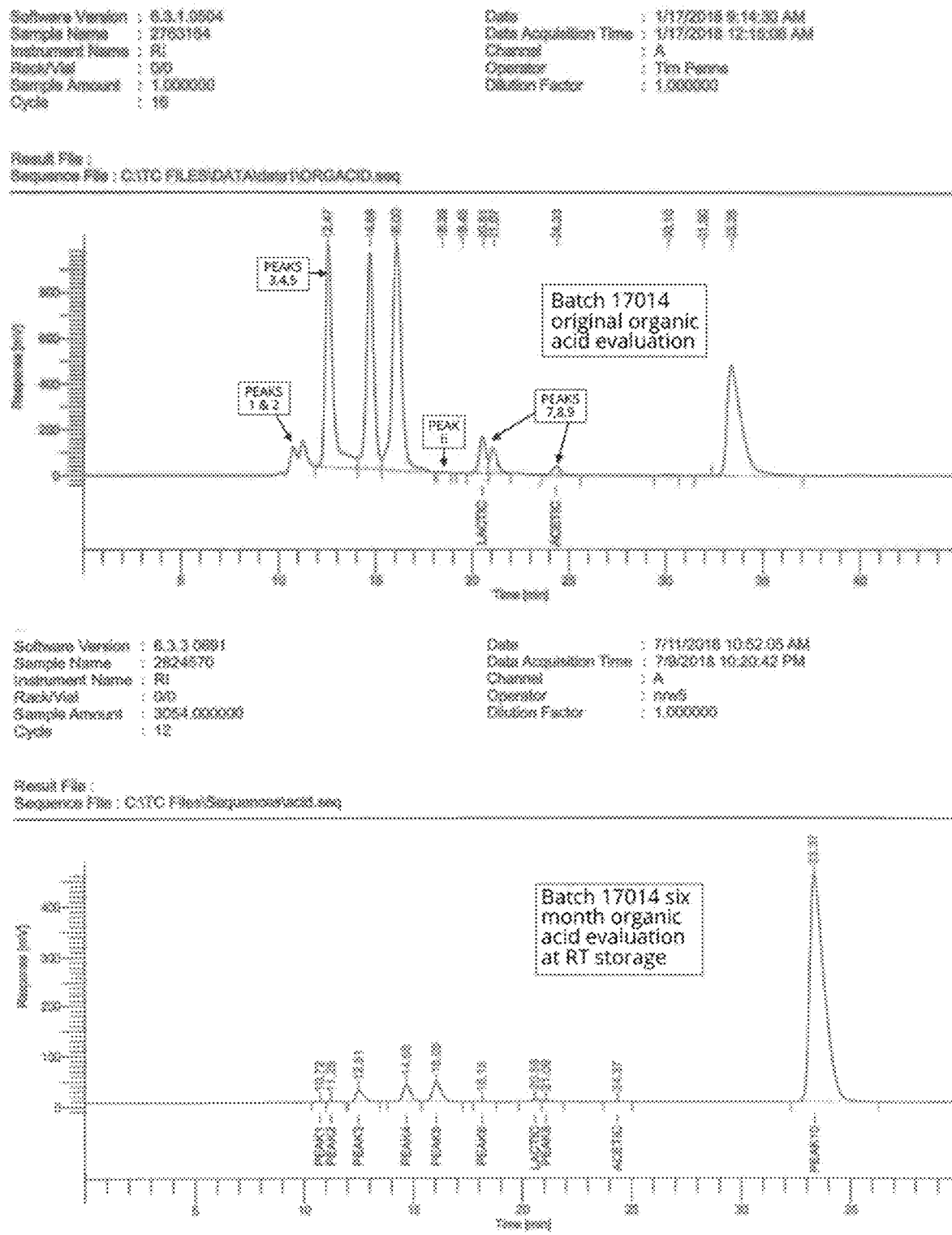
FIG. 8 presents for six month stability tests
Figure 9:
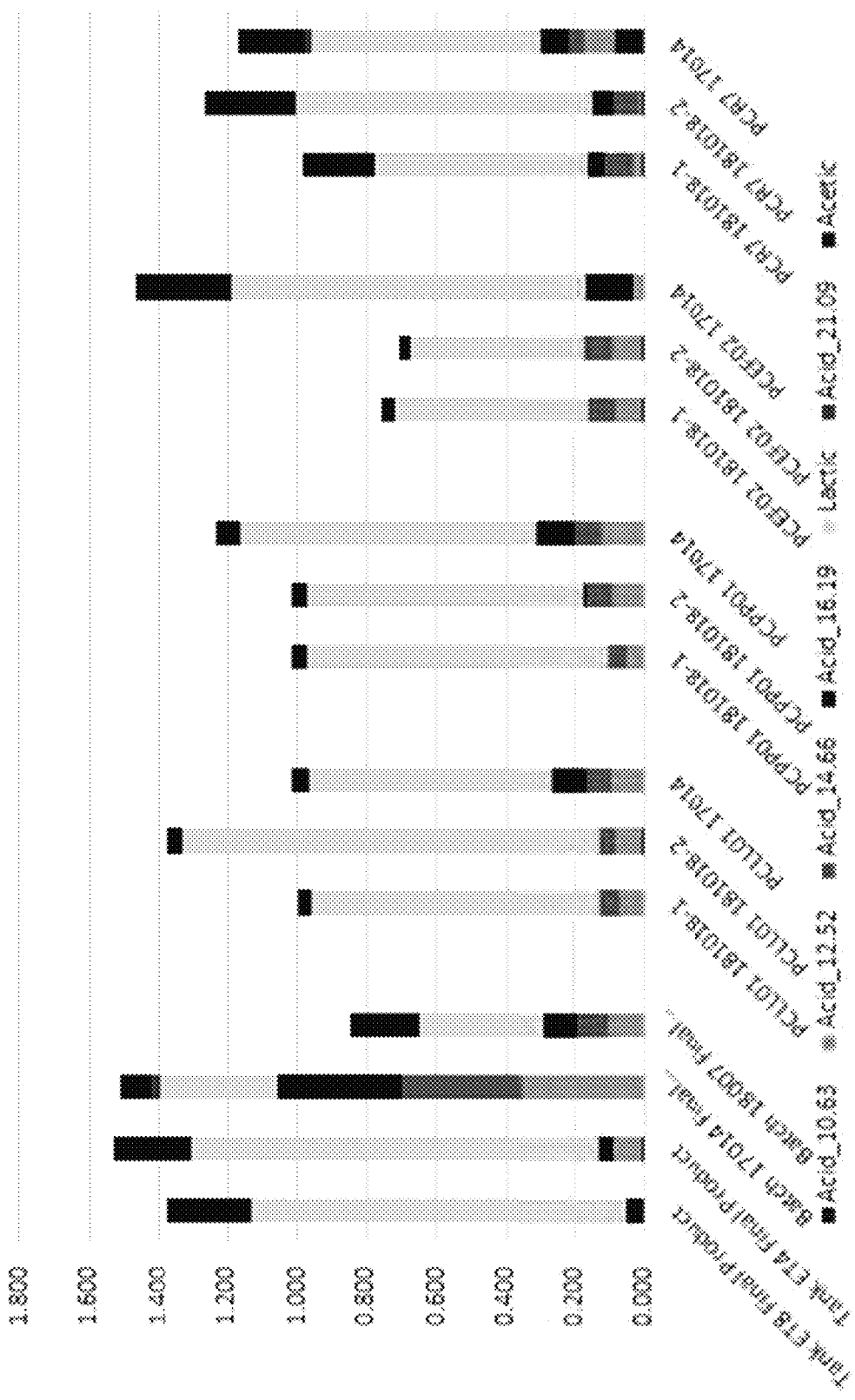
FIG. 9 presents organic acid profile comparisons of compositions and their component strains.

Organic acid chromatography was evaluated for similarities in peaks and areas of each peak present between a sample that was evaluated 5 days after the batch was made against a sample that was six months old and stored at room temperature. Step 1. Determine that there are 9 peaks present in both chromatographs. If there is a new peak present in six month sample ensure that its area is not >1.5% of all areas added together. Step 2. Ensure that the area of peaks 3,4 and 5 are in the ratio of 1:1:1. Step 3. Verify that the lactic acid and acetic acid concentrations in six month sample are +/−0.5% of the concentration of the original sample. Results are shown in FIG. 8.

Example 19

Drying Stability Tests

Formulation 17003 containing strains *Lactobacillus reuteri* PCR7, *Lactobacillus fermentum* PCLF01, and *Enterococcus faecium* PCEF01 in a molasses media was sent to Bluegrass Dairy for spray drying and roller drum drying. Using techniques standard to the art of drying. It was necessary to add nearly 85% w/w maltodextrin for both drying processes.

After drying process samples were sent to Midi Laboratories in Omaha, Neb. where Organic Acids were assayed using AOAC 986.13 (mod) assay.

A HPLC method using Agilent 1100 series HPLC unit. A Bio-Rad Organic Acid Analysis Column Aminex HPX-87H Ion Exclusion Column with 0.2 N H2SO4 stationary mobile phase.

Organic acid chromatography was evaluated for similarities in peaks and areas of each peak present between a sample that was the liquid starting material against dried powders from both the spray drying and roller drum processes. Step 1. Determine that the concentration of lactic acid in the dried material is within the theoretical concentration +/−25%. Calculation: Take the lactic acid result in % and multiply by 99 and divide by 85 (the % of dilution with carrier). If Acetic acid is <0.5% in the original liquid it may not be present in dried material as it more susceptible to heat degradation and volatizing when heated.

Example 20

Comparison of Batches and Component Strains

Figure 10:
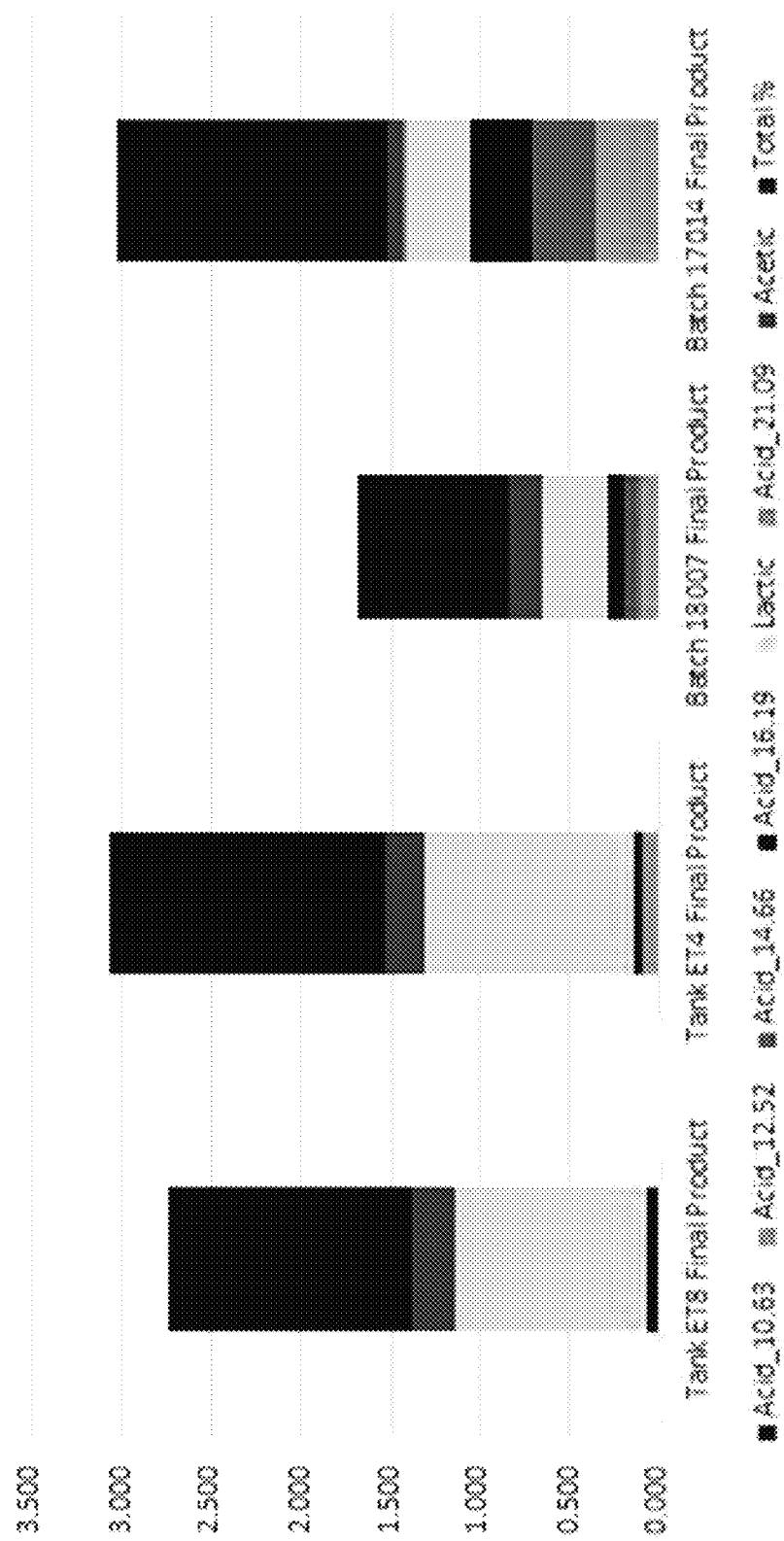
FIG. 10 presents organic acid finger print profiles for batch fermentations.
Figure 11:
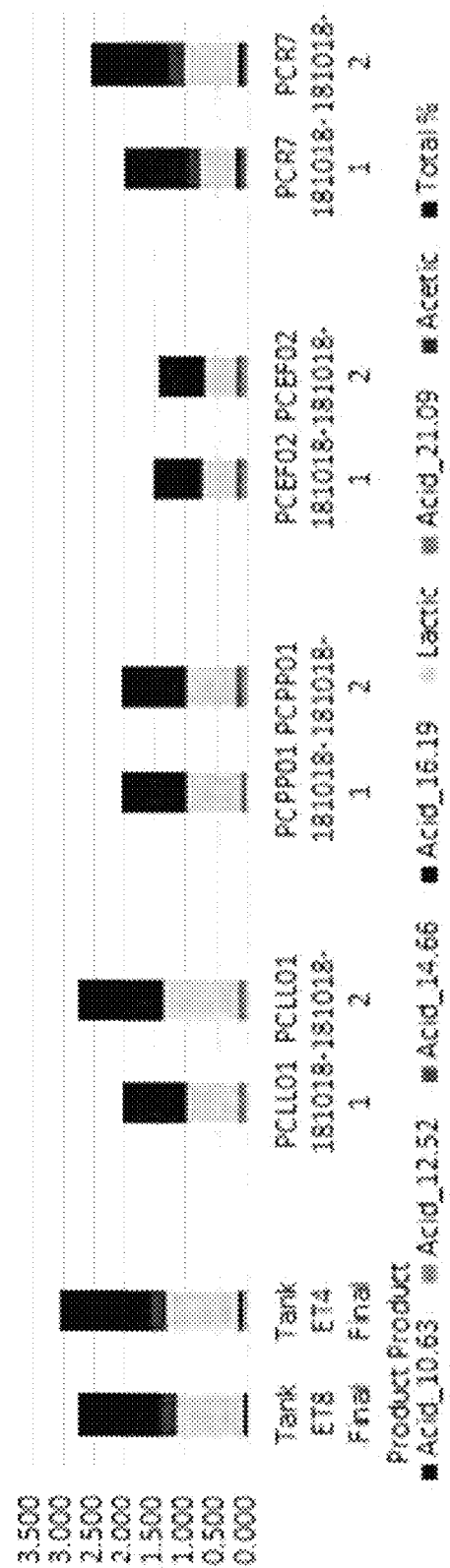
FIG. 11 presents organic acid finger print profiles for batch fermentations compared between two compositions and their component strains.

Organic acid profiles for certain multi strain batches were determined using the methods described above with respect to Example 18. Comparisons between 4 compositions and their components are shown in FIG. 10. FIG. 11 depicts an organic acid "fingerprint" profile for four compositions. FIG. 12 depicts a comparison of certain compositions and component strains. ET8 contains strains *Lactobacillus reuteri* PCR7, *Pediococcus acidilactici* PCLL01, *Pediococcus pentosaceus* PCPP01, *Enterococcus faecium* PCEF02. ET4 contains strains *Lactobacillus reuteri* PCR7, *Pediococcus acidilactici* PCLL01, *Pediococcus pentosaceus* PCPP01, *Enterococcus faecium* PCEF02.

REFERENCES

American Meat Institute (2013). The Facts About Antibiotics in Livestock & Poultry Production. American Meat Institute website. Available from URL: <https://www.meatinstitute.org/Index.phpCDC>. (2013). Center for Disease Control and Prevention. Retrieved from Antibiotic ResistanceThreats Report and Foodborne Germs: http://www.cdc.gov/narms/resources/threats.html.

CDC. (2013). Center for Disease Control and Prevention. Retrieved from Antibiotic Resistance Threats Report and Foodborne Germs: http://www.cdc.gov/narms/resources/threats.html.

Cheng-Hsun Chiu, M. P.-L.-H.-H.-J.-S.-Y. (2002). The Emergence in Taiwan of Fluoroquinolone Resistance in *Salmonella enterica* Serotype Choleraesuis. N Engl J Med, 413-419. Department of Health and Human Services (US), Food and Drug Administration Guidance from industry: New Animal Drugs and New Animal Drug Combination Products Administered in or on Medicated Feed or Drinking Water of Food Producing Animals: Recommendations for Drug Sponsors for Voluntarily Aligning Product Use Conditions with GFI #209. Available from URL: <http://www.fda.gov/downloads/AnimalVeterinary/GuidanceComplianceEnforcement/Guidancefor>Industry/UCM299624.pdf>.

David G. White, P. S. (2001). The Isolation of Antibiotic-Resistant *Salmonella* from Retail Ground Meats. N Engl J Med, 1147-1154.

FDA. (2014, 12). Withdrawal of Enrofloxacin for Poultry. Retrieved from US Department of Health and Human Services: http://www.fda.gov/AnimalVeterinary/SafetyHealth/RecallsWithdrawals/ucm042004.htm.

Gundogan N., Citak S., Yucel N., Devren A. (2005) A note on the incidence and antibiotic resistance of Staphylococcus aureus isolated from meat and chicken samples. Meat Sci 2005; 69:807-10.

Hassan H. M. A., Mohamed M. A., Youssef A. W., Hassan E. R. (2010). Effect of using organic acids to substitute antibiotic growth promoters on performance and intestinal Landers, Timothy F. Landers, Cohen, Bevin, Wittum, Thomas E., Larson, Larson 1., (2012). A Review of Antibiotic Use in Food Animals: Perspective, Policy, and Potential. Public Health Rep. January-February; 127(1): 4-22.

Izat, A., Tidwell, N., Thomas, R., Reiber, M., Adams, M., Colberg, M., & Wadroup, P. (1990). Effects of a buffered propionic acid in diets on the performance of broiler chickens and on the microflora of the intestine and carcass. Poultry Science, 818-826.

Kanehisa M., Goto S. (2000) "KEGG: Kyoto Encyclopedia of Genes and Genomes". Nucleic Acids Res. 28 (1): 27-30.

Luckstadt, C., & Theobald, P. (2011). Dose dependent effects of diformate on broiler performance. In C. Luckstadt, Standards of Acidifiers—Principals for the use of organic acidsin animal nutrition (pp. 83-87). Nottingham: Nottingham University Press.

Manning G., Whyte D. B., Martinez R., Hunter, T. Sudarsanam S. (2002). The protein kinase complement of the human genome. Science, 298 (5600): 1912-1934.

McKenna, Maryn. (2017) Big Chicken. Washington, D.C., National Geographic Partners. Page 31.

Monika Buczek. (2016). Antibiotics in our Food: A complex problem that needs a solution. American society for Microbiology. Available from URL: https://www.asm.org/index.php/general-science-blog/item/72-antibiotics-in-our-food-a-complex-problem-that-needs-a-complex-solution.

Mroz, Z. (2005). Organic acids as potential alternatives to to antibiotic growth promoters for pigs. Advances in Pork Production, 169-182.

PBS Frontline. (2014). Is Your Meat Safe? Modern Meat: Antibiotic Debate Overview. Retrieved Aug. 1, 2015, from PBS Frontline Website: http://www.pbs.org/wgbh/pages/frontline/shows/meat/safe/overview.html.

Phillips I., Casewell M., Cox T., De Groot B., Friis C., Jones R., et al. (2004). Does the use of antibiotics in food animals pose a risk to human health? A critical review of published data. J. Antimicrob. Chemother. 53, 28-52. 10.1093/j ac/dkg48.

Raymond M. J., Wohrle R. D., Call D. R. (2006). Assessment and promotion of judicious antibiotic use on dairy farms in Washington State. J Dairy Sci; 89:3228-40

Sanchez, B., Bressollier, P. and Urdaci, M. C. (2008). Exported proteins in probiotic bacteria: adhesion to intestinal surfaces, host immunomodulation and molecular cross-talking with the host. FEMS Immunology & Medical Microbiology, 54: 1-17. doi:10.1111/j.1574-695X.2008.00454.x.

Szklarczyk D., Franceschini A., Wyder S., Forslund K., Heller D., Huerta-Cepas J., Simonovic M., Roth A., Santos A., Tsafou K. P., Kuhn M., Bork P., Jensen L. J., von Mering C. (2015). "STRING v10: protein-protein interaction networks, integrated over the tree of life". Nucleic Acids Res. 43 (Database issue): D447-52.

Teillant, A. a. (2015). Economics of Antibiotic Use in US Swine and Poultry Production. ChoicesMagazine. Available from URL www.choicesmagazine.org/UserFiles/file/cmsarticle_404.pdf.

Teillant, A. a. (2015). Economics of Antibiotic Use in US Swine and Poultry Production. Choices, pp. 1-11.

Trost B., Kindrachuk J., Määttänen P., Napper S., Kusalik A. (2013) PIIKA 2: An Expanded, Web-Based Platform for Analysis of Kinome Microarray Data. PLOS ONE 8(11): e80837.https://doi.org/10.1371/journal.pone.0080837.

Urdaneta, D., Raffe, D., Ferrer, A., Sulbarán de Ferrer, B., Cabrera, L., & Pérez, M. (1995). Short-chain organic acids produced on glucose, lactose, and citrate media by *Enterococcus faecalis*, *Lactobacillus casei*, and *Enterobacter aerogenes* strains. Bioresource Technology, 99-103.

Zalán, Z., Hudáček, J., Štětina, J., Chumchalová, J., & Halász, A. (2009). Production of organic acids by Lactobacillus strains in three different media. European Food Research and Technology, 395-404.

All cited references are herein expressly incorporated by reference in their entirety for their relevant disclosure.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth OPT or shown in the accompanying drawings are to be interpreted as illustrative, and not in a limiting sense.

While specific embodiments have been shown and discussed for purposes of illustration, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A composition comprising microbes comprising *Lactobacillus reuteri* PCR7, *Pediococcus acidilactici* PCLL01, *Enterococcus faecium* PCEF02, and *Pediococcus pentosaceus* PCPP01, and metabolites produced by the microbes when grown in combination.

2. The composition of claim 1, wherein the composition further comprises *Lactobacillus fermentum* PCF01.

3. The composition of claim 1, wherein the metabolites comprise a short chain fatty acid selected from the group consisting of acetic acid, formic acid, propionic acid, butyric acid, isobutyric acid, valeric acid, isovaleric acid, succinic acid, and combinations thereof.

4. The composition of claim 1, wherein the metabolites comprise a sugar selected from the group consisting of a 4-carbon sugar, a 5-carbon sugar, a 6-carbon sugar, and combinations thereof.

5. The composition of claim 1, wherein the metabolites comprise an oligosaccharide.

6. The composition of claim 5, wherein the oligosaccharide is selected from the group consisting of a fructooligosaccharide, a galactooligosaccharide, a xylooligosaccharide, an isomaltooligosaccharide, an inulin oligosaccharide, a mannanoligosaccharide, and combinations thereof.

7. The composition of claim 1, wherein the metabolites comprise a bacteriocin.

8. The composition of claim 7, wherein the bacteriocin is selected from the group consisting of acidophilin, acidolin or reutericin.

9. The composition of claim 1, wherein the metabolites comprise metabolites produced when the microbes are grown in a medium comprising molasses.

10. The composition of claim 9, wherein the medium additionally comprises glycerol and a prebiotic selected from an inulin and fos.

11. The composition of claim 1, wherein a portion of the microbes are viable after storage at room temperature for 2.2 months at greater than 50,000,000 cfu/ml.

12. The composition of claim 1, wherein an organic acid profile of the composition is stable after storage for six months at room temperature.

13. The composition of claim 1, wherein an organic acid profile of the composition is stable when the composition is heated to 90° C. for 6 minutes.

14. The composition of claim 1, wherein an organic acid profile of the composition is stable after roller drying and/or spray drying the composition.

15. A method of treating or preventing a disease or condition in an animal in need thereof, the method comprising administering to the animal the composition of claim 1.

16. The method of claim 15, wherein the disease or condition is a gastrointestinal disease.

17. The method of claim 15, wherein the disease or condition is necrotic enteritis, *Salmonella* enteritis, or coccidiosis mastitis.

18. The method of claim 15, wherein the disease or condition is caused by an infectious microbial agent.

19. The method of claim 18, wherein the disease or condition is caused by a *Clostridium* species.

20. The method of claim 15, wherein the composition modulates a gastrointestinal microbiome of the animal.

21. The method of claim 15, wherein the composition modulates a gastrointestinal immune response of the animal.

22. The method of claim 15, wherein the composition modulates a phosphorylation of gastrointestinal proteins of the animal.

23. The method of claim 15 wherein the composition is provided in a solid form, and included in an animal feed ration at a concentration of from about 0.25 kg/ton to about 2.0 kg/ton of feed.

24. The method of claim 15, wherein the composition is formulated into a liquid form and added to a drinking water system of the animal.

25. The method of claim 15, wherein the composition is dosed from about 0.4 mL per animal per day to about 5.0 mL per animal per day.

26. The method of claim 15, wherein the composition is formulated to contain a lactic acid bacterial count of at least about $1.0 \times 10^5$.

* * * * *